United States Patent
Georgakoudi et al.

(10) Patent No.: US 9,952,148 B2
(45) Date of Patent: Apr. 24, 2018

(54) NON-INVASIVE OPTICAL CHARACTERIZATION OF BIOMATERIAL MINERALIZATION

(75) Inventors: Irene Georgakoudi, Acton, MA (US); Sharad Gupta, Medford, MA (US); Martin Hunter, Bradford, MA (US); David L. Kaplan, Concord, MA (US)

(73) Assignee: Trustees of Tufts College, Boston, MA (US)

( * ) Notice: Subject to any disclaimer, the term of this patent is extended or adjusted under 35 U.S.C. 154(b) by 1461 days.

(21) Appl. No.: 12/867,383

(22) PCT Filed: Feb. 19, 2009

(86) PCT No.: PCT/US2009/034516
§ 371 (c)(1),
(2), (4) Date: Nov. 19, 2010

(87) PCT Pub. No.: WO2009/105537
PCT Pub. Date: Aug. 27, 2009

(65) Prior Publication Data
US 2011/0109910 A1 May 12, 2011

Related U.S. Application Data

(60) Provisional application No. 61/029,827, filed on Feb. 19, 2008.

(51) Int. Cl.
*G01N 21/47* (2006.01)
*G01N 21/21* (2006.01)

(52) U.S. Cl.
CPC ............ *G01N 21/47* (2013.01); *G01N 21/21* (2013.01); *G01N 2021/4792* (2013.01)

(58) Field of Classification Search
CPC ............... G01N 2015/1493; G01N 2021/0346
(Continued)

(56) References Cited

U.S. PATENT DOCUMENTS

| 4,479,499 A | * | 10/1984 | Alfano | A61B 5/0088 356/317 |
| 4,836,206 A | | 6/1989 | Maxwell et al. | |

(Continued)

FOREIGN PATENT DOCUMENTS

WO   2009105537   9/2009

OTHER PUBLICATIONS

Hunter et al. "Tissue Self-Affinity and Polarized Light Scattering in the Born Approximation: A New Model for Precancer Detection", Physical Review Letters 97, Sep. 29, 2006.*
(Continued)

*Primary Examiner* — Dominic J Bologna
(74) *Attorney, Agent, or Firm* — Thomas J. Engellenner; Reza Mollaaghababa; Pepper Hamilton LLP

(57) ABSTRACT

In one aspect, the present invention generally provides methods for characterizing mineralization of a material, e.g., a biomaterial, by illuminating the material with radiation and analyzing radiation scattered from the material in response to the illumination. For example, in some embodiments, a material can be illuminated with polarized radiation at a plurality of wavelengths and the elastically scattered radiation corresponding to two or more of those wavelengths can be collected at two polarizations: one parallel and the other perpendicular to the illumination polarization. A differential intensity of the scattered radiation at the two polarizations can be analyzed as a function of wavelength to obtain information regarding the morphology of mineral deposits in the sample. Further, the total scattered radiation can be analyzed to derive information regarding the level of mineralization.

22 Claims, 26 Drawing Sheets

(58) Field of Classification Search
USPC .......................... 356/73, 446, 456, 301, 343
See application file for complete search history.

(56) References Cited

U.S. PATENT DOCUMENTS

| | | | |
|---|---|---|---|
| 5,009,102 A | 4/1991 | Afromowitz | |
| 5,452,723 A * | 9/1995 | Wu .................... | A61B 5/0059 250/340 |
| 6,091,984 A | 7/2000 | Perelman et al. | |
| 6,122,042 A * | 9/2000 | Wunderman et al. .......... | 356/73 |
| 6,404,497 B1 | 6/2002 | Backman et al. | |
| 6,697,652 B2 * | 2/2004 | Georgakoudi ....... | A61B 5/0059 356/342 |
| 7,264,794 B2 | 9/2007 | Georgakoudi et al. | |
| 7,796,243 B2 * | 9/2010 | Choo-Smith ........ | A61B 5/0066 356/72 |
| 2002/0093655 A1 * | 7/2002 | Everett ................ | A61B 5/0073 356/369 |
| 2003/0137669 A1 * | 7/2003 | Rollins .............. | G01B 11/2441 356/479 |
| 2005/0073681 A1 * | 4/2005 | Sevick-Muraca et al. ... | 356/336 |
| 2005/0283058 A1 * | 12/2005 | Choo-Smith ........ | A61B 5/0088 600/315 |
| 2007/0133002 A1 * | 6/2007 | Wax ..................... | A61B 5/0075 356/456 |
| 2009/0021724 A1 * | 1/2009 | Mahadevan-Jansen et al. ........................ | 356/73 |

OTHER PUBLICATIONS

Kong et al. "Silk fibroin regulated mineralization of hydroxyapatite nanocrystals" Journal of Crystal Growth, vol. 270, Issues 1-2, Sep. 15, 2004.*

Kim, et al., "Simultaneous Measurement of Angular and Spectral Properties of Light Scattering for Characterization of Tissue Microarchitecutre and Its Alteration in Early Precancer", IEEE, vol. 9, No. 2 (2003).

* cited by examiner

NON-INVASIVE OPTICAL CHARACTERIZATION OF BIOMATERIAL MINERALIZATION

RELATED APPLICATION

The present application claims priority to a provisional application entitled "Non-Invasive Optical Characterization Of Biomaterial Mineralization" having a Ser. No. 61/029,827 filed on Feb. 19, 2008, which is herein incorporated by reference.

GOVERNMENT SUPPORT

This invention was made with government support under NSF (BES 0547292) and NIH (Tissue Engineering Resource Center P41 EB002520, and RO1CA097966). The U.S. government has certain rights in this invention.

BACKGROUND

The present invention relates generally to methods for obtaining information regarding mineral constituent(s) of a sample, and more particularly to such methods that employ radiation scattering to derive information regarding mineralization of a sample.

Nature synthesizes hierarchical, self-assembled, organic/biomineral complex composites under ambient conditions with superior mechanical properties. In general, biomineralization can be divided into two categories: biologically induced mineralization in which an organism modifies its local microenvironment to establish conditions suitable for the chemical precipitation of extracellular mineral phases, and boundary organized biomineralization in which inorganic particles are grown within or on a matrix generated by an organism. While biologically induced mineralization can typically result in mineral particles with a broad size distribution and without a unique morphology, boundary organized biomineralization can provide better control over size, morphology and crystallographic orientation of the mineralized particles. In either case, the central tenet in the regulation of mineral deposition in biological systems is that organic matrices control the nucleation and growth of inorganic structures. Such control can be exerted through the use of organic macromolecules that can provide nucleation sites and dictate crystal orientation and morphology. However, these processes are not well understood.

Human bones and teeth are examples of bio-mineralized tissues that are formed by the deposition of hydroxyapatite on aligned collagen fibers. Hydroxyapatite formation and deposition is a key element for bone defect repair. The human body is able to repair minor injuries of bones, but such natural repair mechanisms typically do not work efficiently in case of large injuries or damaged self-reconstruction. In such cases, autografts and allografts may be used for the replacement of the damaged part. But autografts and allografts have certain drawbacks. For example, autografts can be limited by the availability of the size of usable bone and allografts can carry risks of disease transfer, infections and adverse immunological response. As such, the fabrication and use of bone tissue and implant has been an active area of research. Biomaterial scaffolds are used as three-dimensional extracellular matrices to engineer bone tissue and bone implant. For example, silk is one of the most promising scaffolding materials for tissue engineering due to its biocompatibility and advantageous mechanical properties. To have a better control over the functionality of engineered bone, tools for studying the mineralization process are needed.

Scanning electron microscopy (SEM) has been traditionally used as a characterization technique to study the detailed surface topography and crystal morphology of the mineral deposits. However, SEM is an invasive technique, as are most of the other commonly used methods to study mineralized samples, such as X-ray diffraction, X-ray photoelectron spectroscopy (XPS), and transmission electron microscopy (TEM). As such, these techniques are not particularly suited for time-dependent measurements at different mineralization stages of a sample under study.

Fourier transform infrared (FTIR) spectroscopy is a non-invasive technique that has been used for molecular characterization of mineral samples. But it lacks the ability to provide morphological information. Further, its use is generally limited in samples having a high water content, such as biological tissue.

In biomedical imaging for bone formation, micro computed tomography or X-ray analysis are most often employed to assess bone density and mineral distribution. These techniques, however, lack the resolution typically needed to understand fine control of mineralization. Nor do they provide sufficient sensitivity to assess early stages of mineralization.

Hence, there is a need for enhanced methods for monitoring and quantifying mineralization processes.

SUMMARY OF THE INVENTION

In one aspect, a method of monitoring mineralization is disclosed that includes illuminating a sample with radiation, detecting at least a portion of the radiation scattered from the sample in response to the illumination and analyzing the scattering data acquired at two or more different wavelengths (corresponding to two or more excitation wavelengths) and/or two or more different scattering angles to obtain information regarding one or more mineral constituents of the sample. In many embodiments, the detected scattered radiation at each excitation wavelength corresponds to elastically scattered radiation. The information obtained can relate, for example, to the morphology of one or more mineral constituents of the sample and/or their organization.

In many embodiments, polarized radiation can be used to illuminate the sample. Scattered radiation having a polarization parallel and perpendicular to the illuminating polarization can be detected. A differential signal corresponding to a difference between the intensities of the detected scattered radiation at those two polarizations can be analyzed as a function of wavelength to derive information about one or more mineral constituents of the sample.

In some embodiments, the sample can be illuminated concurrently with two or more radiation wavelengths, and the collected scattered radiation can be dispersed to obtain the intensity of the scattered radiation at each of those wavelengths. In other embodiments, the sample can be illuminated with each of a plurality wavelengths during different temporal intervals. In other embodiments, the sample can be illuminated with one or more radiation wavelengths, and the collected scattered radiation can be dispersed to obtain the intensity of the scattered radiation at each of these wavelengths as a function of the scattering angle. As noted above, in many embodiments, the detected scattered radiation corresponds to radiation that is elastically scattered from the sample in response to the excitation radiation.

The method can further include calculating, for each of the wavelengths and/or scattering angles, a differential intensity of the detected scattered radiation at the parallel and perpendicular polarizations. Differential intensity corresponding to one wavelength and/or angle can be compared with the respective differential intensity corresponding to the other wavelength and/or angle to obtain the information regarding the one or more mineral constituents of the sample.

In another aspect, a method of measuring a property of a sample is disclosed including measuring a wavelength and/or scattering angle spectrum of radiation scattered from a sample in response to illumination of the sample by radiation having a plurality of wavelengths, and utilizing the wavelength and/or scattering angle spectrum to derive information regarding mineralization of the sample. The method can further include fitting the wavelength and/or scattering angle spectrum to a morphological mineralization model to derive information regarding morphology of one or more mineral constituents of the sample. In some embodiments, the method further includes integrating the wavelength and/or angle spectrum to obtain information regarding an amount of one or more mineral constituents of the sample.

In a related aspect, the invention discloses a method of monitoring a sample including measuring radiation scattered from a sample in response to illumination by radiation at a plurality of wavelengths during each of a plurality of temporal intervals, for each of the temporal intervals, analyzing the measured scattered radiation as a function of wavelength to derive information regarding mineralization of the sample, and comparing the information corresponding to different temporal intervals to monitor changes in the mineralization as a function of time. Similarly, the method can also involve illuminating the sample with radiation of a single or multiple wavelengths and measuring the radiation scattered from the sample at two or more scattering angles during each of a plurality of temporal intervals, for each of the temporal intervals, analyzing the measured scattered radiation as a function of scattering angle to derive information regarding mineralization of the sample, and comparing the information corresponding to different temporal intervals to monitor changes in the mineralization as a function of time.

In some aspects of the present invention, polarized light scattering spectroscopy (LSS) is used as a non-invasive method for assessing the levels of mineralization as well as some aspects of the organization of the mineral deposits. In contrast to currently available approaches to study biomaterial mineralization, which are generally invasive and are not particularly suited for dynamic characterization of this process within the same sample, many embodiments of the methods of the present invention are non-invasive and highly efficient.

In one embodiment, the present invention discloses the use of LSS to characterize the generation of various mineral formations, such as, for example, hydroxyapatite deposits on three types of silk films (water-annealed, methanol-treated and poly aspartic acid (PAA)-mixed) following 1, 3, 5 and 7 cycles of mineralization. The total light scattering intensity can provide a quantitative measure of the degree of mineralization. The methods of the present invention provide a valuable tool for understanding the role of biomaterial properties in mineral formation, and for optimizing biomaterial designs that yield mineral deposits with the desired organization.

In another aspect, a method of characterizing mineralization of a sample is disclosed, which comprises measuring radiation backscattered from a sample at two different polarizations (e.g., at two orthogonal polarizations) in response to illumination of the sample with radiation at a plurality of wavelengths, and obtaining a differential intensity of the measured backscattered radiation at said polarizations for the plurality of wavelengths. The measured differential intensity can be analyzed as a function of wavelength to characterize mineralization of the sample. The characterization of the mineralization can include, e.g., obtaining information regarding the morphology of mineral deposits and/or the degree of mineral deposition.

In some cases, in the above method, a self-affine fractal model can be utilized to derive information regarding morphology of the mineral deposits from the measured backscattered differential intensity. By way of example, the self-affine fractal model can be described by the following expression:

$$\Delta I(\lambda) \propto \lambda^{-4} \frac{1}{[1+(4\pi L/\lambda)^2]^\alpha}$$

wherein,

L represents the fractal upper scale (the upper bound of fractal correlation lengths) and the exponent $\alpha$ is related to the Hurst parameter, H, via the following relation:

$$H = \alpha - D_E/2$$

wherein, $D_E$ is the Euclidean dimension of the scattering system.

By way of example, if fitting the differential backscattered intensity data to the above relation would result in a $D_E=1$, a filamentous morphology for the mineral deposits can be inferred. A derived $D_E=2$ can denote a sheet-like morphology for the mineral deposits, while a $D_E=3$ can denote a bulk space-filling morphology.

In another aspect, a system for characterizing mineralization of a sample is disclosed that includes at least one radiation source for generating radiation at a plurality of wavelengths, and an optical system optically coupled to the source for directing the radiation onto a sample. The system can further include a detection system for detecting radiation backscattered from the sample in response to the radiation directed to the sample, and an analysis module for analyzing the backscattered radiation as a function of wavelength to obtain information regarding one or more mineral constituents of the sample.

In another aspect, the detection system can comprise an analyzer that is coupled to a detector, where the analyzer can selectively permit the passage of backscattered radiation at two different polarizations (e.g., orthogonal polarizations) such that the detector detects the intensity of the backscattered radiation at each of said two different polarizations. The analysis module, which is in communication with the detector, can then determine a differential intensity of the detected backscattered radiation at said two polarizations, and analyze the differential intensity of the backscattered radiation as a function of wavelength to characterize one or more mineral constituents of the sample. For example, the analyzer can be configured to fit the differential scattering data to a self-affine fractal model to derive information regarding the morphology of the mineral constituent(s).

In some cases, the total backscattered intensity, e.g., the backscattered intensity within a solid angle subtended by a detector for all backscattered wavelengths and polarizations, can be utilized to obtain information regarding the degree of mineralization. For example, a greater intensity of the backscattered radiation can indicate a greater degree of mineralization.

DETAILED DESCRIPTION

The present invention generally provides methods for characterizing mineralization of a material, e.g., a biomaterial, by illuminating the material with radiation and analyzing radiation scattered from the material in response to the illumination. For example, in some embodiments, a material can be illuminated with polarized radiation at a plurality of wavelengths and the elastically scattered radiation corresponding to two or more of those wavelengths can be collected at two polarizations: one parallel and the other perpendicular to the illumination polarization. A differential intensity of the scattered radiation at the two polarizations can be analyzed as a function of wavelength and/or scattering angle to obtain information regarding the morphology of mineral deposits in the sample. Further, the total scattered radiation can be analyzed to derive information regarding the level of mineralization. The terms "mineral" and "mineralization" are known in the art. To the extent that any further explanation may be needed, the term "mineral" can refer to any inorganic components that are structurally organized to constitute an intact material phase, for example, a solid phase. For example, such components can be part of a biomaterial. The term "mineral" is intended to cover both naturally occurring and synthetic substances. In some cases, the inorganic solid substance can have a crystalline or polycrystalline structure. The mineral can be a homogenous or a heterogenous substance; however, impurities can occur. For example, in some cases a mineral can include organic impurities of less than about 20% of its total weight, preferably less than about 10%, more preferably less than 5%, most preferably less than about 1%.

The term "mineralization" can refer to any process by which a mineral can be formed. For example, mineralization includes any process where a substance is converted from an organic substance to a substantially inorganic substance.

The term "mineral constituent" refers to the inorganic substances that form the mineral. For example, the mineral constituents can include an aggregate of one or more inorganic substances.

In many embodiments, light scattering spectroscopy (LSS) is utilized as a non-invasive tool to characterize the amount and/or organization of mineral deposits in a sample by examining the light scattered from scattering structures having a different refractive index from that of their surrounding as a function of wavelength and/or scattering angle to obtain information regarding the size, shape and refractive index of the scatterers.

Figure 1:
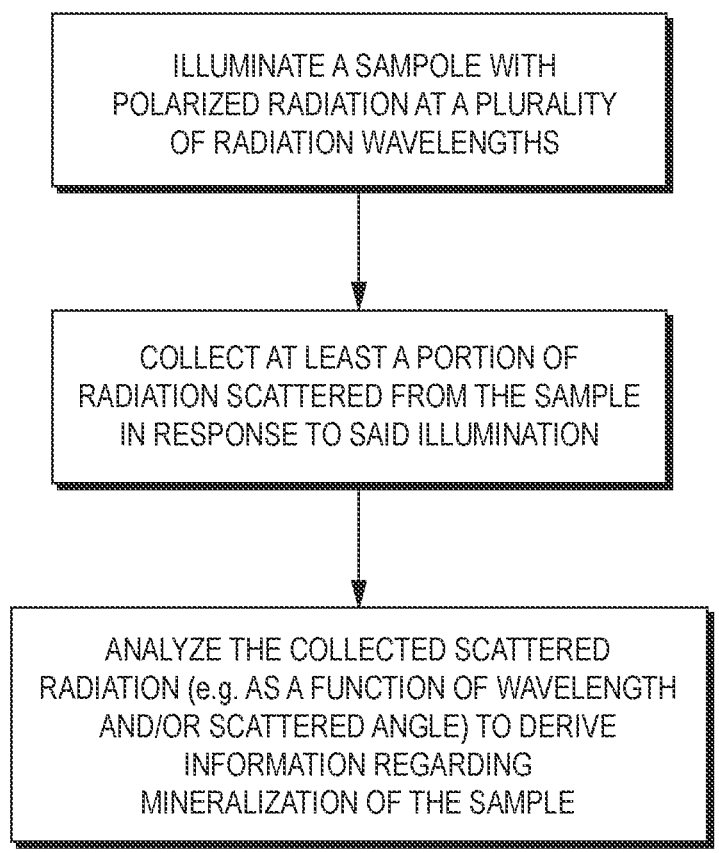
FIG. 1 is a flow chart depicting various step of an embodiment of a method according to the invention for measuring mineralization of a sample.

With reference to the flow chart of FIG. 1, in a method according to an embodiment of the invention, a sample under study can be illuminated with linearly polarized radiation at a plurality of radiation wavelengths (step 1). The radiation scattered from the sample in response to the illuminating radiation can be collected (step 2) and analyzed to derive information (step 3) regarding mineralization of the sample (e.g., mineral content and/or morphology of mineral constituent(s) (e.g., mineral deposits) of the sample). In many cases, the backscattered radiation is collected and analyzed to obtain such information. The term "backscattered radiation" is known in the art. To the extent that any further explanation may be needed, it refers to scattered radiation propagating in directions that are generally opposite to the propagation direction of the excitation radiation. The backscattered direction can propagate along a direction that is exactly opposite to that of the excitation radiation, or alternatively, it can propagate along a direction that forms a non-zero angle (e.g., greater than zero, where zero is defined as the exact backward direction, and equal to or less than 90 degrees) relative to the propagation direction of the excitation radiation.

By way of example, in some cases, polarized radiation incident on the sample can be generated by optically coupling radiation from a broad bandwidth source characterized by a plurality of wavelengths (e.g., it can be white light) to one or more polarizers. In many embodiments, the excitation (illuminating) radiation can have wavelengths in a range of about 450 nm to about 700 nm. The elastically scattered radiation corresponding to two orthogonal polarizations (e.g., one parallel to the polarization of the incident radiation and the other perpendicular to the incident polarization) can be detected at a number of wavelengths. For example, the backscattered radiation at each polarization can be dispersed, e.g., by utilizing a diffraction grating, to obtain information regarding intensity of scattered radiation as a function of wavelength. Alternatively, in some other cases, a source generating a narrow bandwidth radiation (e.g., a laser) can be tuned over a selected wavelength range to illuminate the sample with radiation at a plurality of wavelengths at successive temporal intervals. The scattered radiation at each wavelength can be detected to generate a wavelength spectrum of the scattered radiation. In some embodiments the scattered radiation at one or more wavelengths can be detected at two or more scattering angles to generate a scattering angle-dependent spectrum. In some embodiments, such a wavelength and/or scattering-angle spectrum can be generated for two orthogonal polarizations: one parallel and the other perpendicular to the polarization axis of the incident radiation.

In some embodiments, following the detection of the scattered radiation at a plurality of wavelengths and/or scattering angles, the differential intensity of the detected scattered radiation at the two polarizations can be analyzed as a function of wavelength and/or scattering angle to obtain information regarding mineralization of the sample. Such a differential intensity at a wavelength ($\lambda$) of the scattered radiation ($\Delta I$) can be defined mathematically as follows:

$$\Delta I = I_{par} - I_{perp} \qquad \text{Eq. (1)}$$

wherein $I_{par}$ represents scattered radiation intensity with a polarization parallel to that of the incident radiation, $I_{perp}$ represents scattered radiation intensity with a polarization perpendicular to that of the incident radiation.

The use of such a differential intensity can be advantageous as it predominately provides information regarding radiation that has undergone a single or very few scattering events rather than multiple scattering events, as discussed further below. This is useful for ensuring that the information contained within the wavelength or scattering angle-dependent light scattering spectrum is representative of the most superficial layer of the sample.

As noted above, the variation of the differential intensity as a function of wavelength and/or scattering angle can be utilized to derive information regarding the morphology of mineral deposits in the sample. By way of example, in some cases the data corresponding to differential scattering intensity at a plurality of wavelengths and/or scattering angles can be fitted to a morphological model having one or more adjustable parameters so as to obtain values for those parameters. The derived values of the parameters can in turn provide information regarding the morphology of mineral deposits in the sample. Examples of such morphological information can include, without limitation, fractal topology, the size scale and/or size distribution, the spatial arrangements of various crystalline and/or amorphous domains of the mineral constituent(s) and their orientation and packing depending on the biomaterial substrate.

By way of example, in some cases, the differential wavelength-dependent scattering data can be analyzed by employing a model that assumes self-affine fractal morphology of a plurality of scatterers (i.e., mineral deposits). As is known in the art, a characteristic property of a fractal object is scale invariance. In the case of a self-similar fractal, the scale invariance is isotropic (an object appears indistinguishable at varying scales), whereas self-affinity implies anisotropic scale invariance. A self-affine fractal function $f(x)$ can have a variance $S(x)=<|f(x+a)-f(x)|^2>$, which scales according to $S(bx) \propto b^H S(x)$, where H represents the Hurst parameter, which is limited to the range 0<H<1. In self-similar fractals, scale invariance often results from a highly organized, iterative regenerative process (e.g., the progressive branching in fern leaves or human lung architecture). Self-affinity, on the other hand, is associated with random (or quasi-random) processes. Brownian motion, for example, is a self-affine process. Fractional values of the Hurst parameter H smaller than, or greater than, H=0.5 imply, respectively, varying degrees of persistence (positive correlations), or anti-persistence (negative correlations), superimposed on an underlying random process.

In some embodiments, a self-affine fractal model utilized to analyze the wavelength dependence of the differential scattering data ($\Delta I(\lambda)$) can be described by the following relation:

$$\Delta I(\lambda) \propto \lambda^{-4} \frac{1}{[1+(4\pi L/\lambda)^2]^\alpha} \qquad \text{Eq. (2)}$$

wherein

L represents the fractal upper scale (the upper bound of fractal correlation lengths), and α is related to the Hurst parameter, H, by the following relation:

$$H=\alpha-D_E/2 \qquad \text{Eq. (3)}$$

wherein, $D_E$ is the Euclidean dimension of the scattering system (i.e., $D_E$=1, 2, or 3).

In some embodiments, the angular dependence of the scattered radiation as well as its wavelength dependence can be analyzed to obtain information about the mineral constituent(s) of a sample. For example, backscattered radiation can be collected at a plurality of angles, e.g., ranging from zero (corresponding to a direction substantially parallel to a vector normal to a surface of the sample that exposed to illuminating radiation) to about 90 degrees (corresponding to a direction substantially perpendicular to a vector normal to the sample surface that is exposed to illuminating radiation). In some cases, for each angle, the intensity of the scattered radiation can be determined at a plurality of wavelengths (or over a wavelength range).

As discussed above, the wavelength dependence of the scattered radiation at each scattering angle can provide information regarding the morphology of mineral deposits in the sample. Similar information can be acquired by analyzing the scattering angle dependence of the scattered radiation at a single or multiple wavelengths. This information can be further refined by comparison of wavelength-dependent scattering intensities corresponding to different scattering angles. For example, the parameters of a model, such as that discussed above, obtained from the dependence of the scattering data on wavelength at different scattering angles can be compared to further refine the information regarding the morphology of the mineral deposits. By way of further example, in some cases, a map of scattered intensity data corresponding to a plurality of scattering wavelengths and scattering angles can be generated and utilized to obtain information regarding the morphology of the mineral deposits. Further, the scattering data corresponding to different scattering wavelengths and angles can be employed to quantify the amount of mineral deposits (e.g., by weight percent) in the sample. By way of example, this can be done by integrating the two-dimensional scattering data corresponding to different angles and wavelengths.

Figure 2:
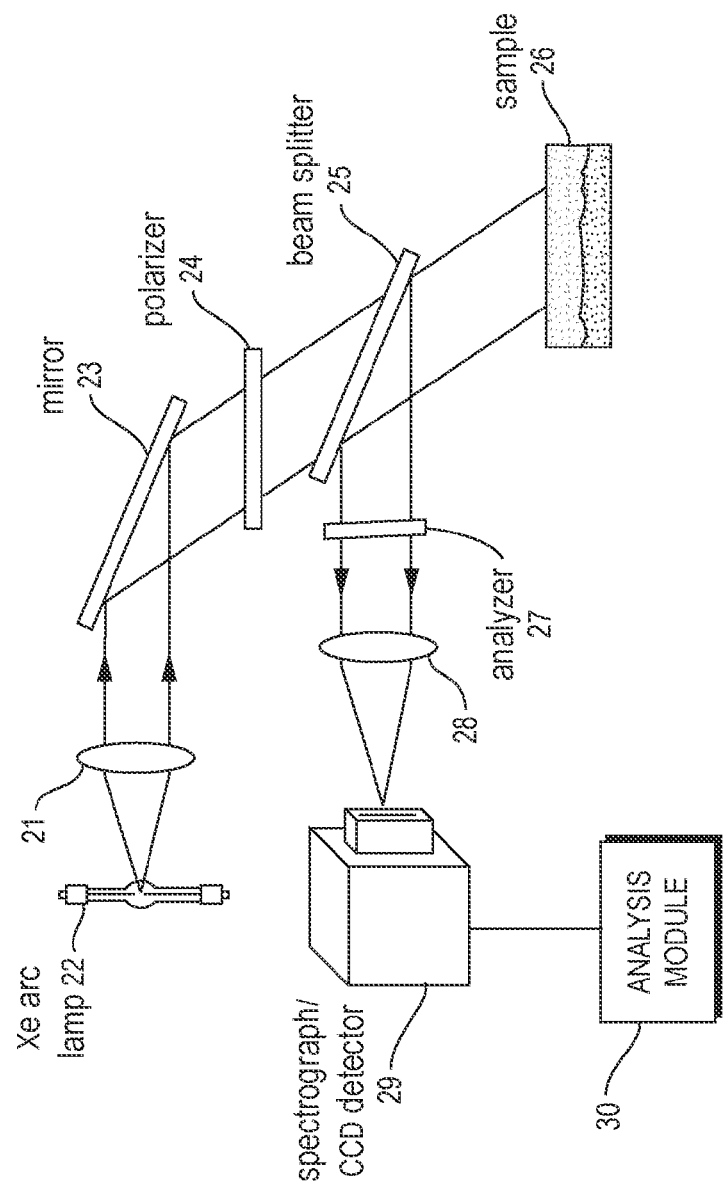
FIG. 2 schematically depicts an apparatus for performing measurements according the methods of the invention.
Figure 3A:
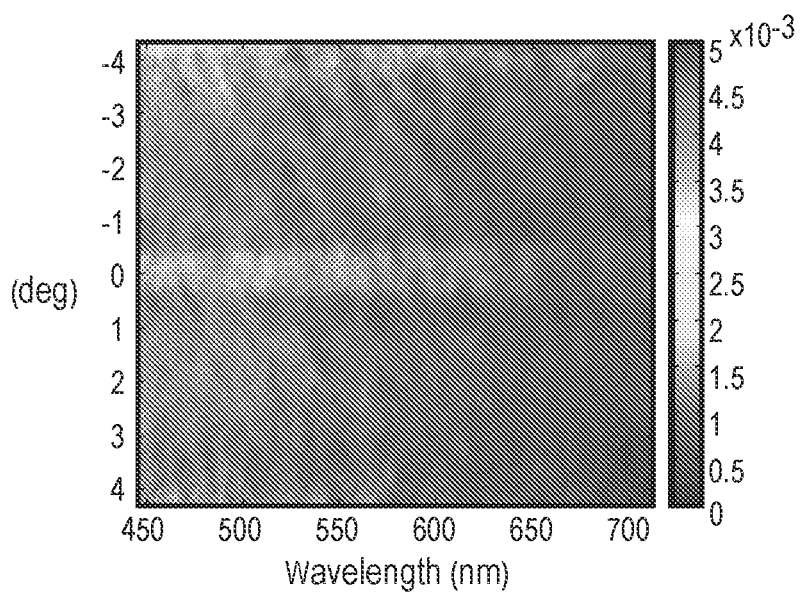
FIG. 3A shows a differential light scattering map of a silk film before mineralization.
Figure 3B:
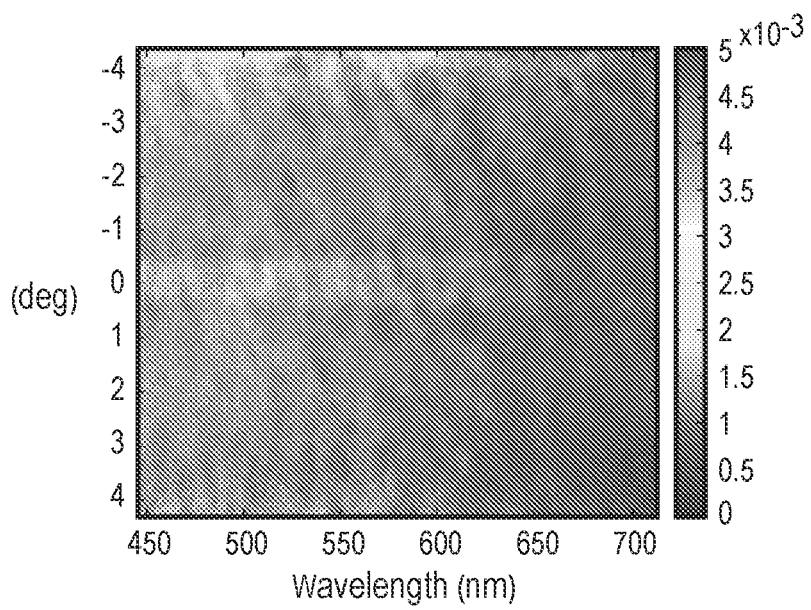
FIG. 3B shows a differential light scattering map of the silk film after 2 days of mineralization.
Figure 3C:
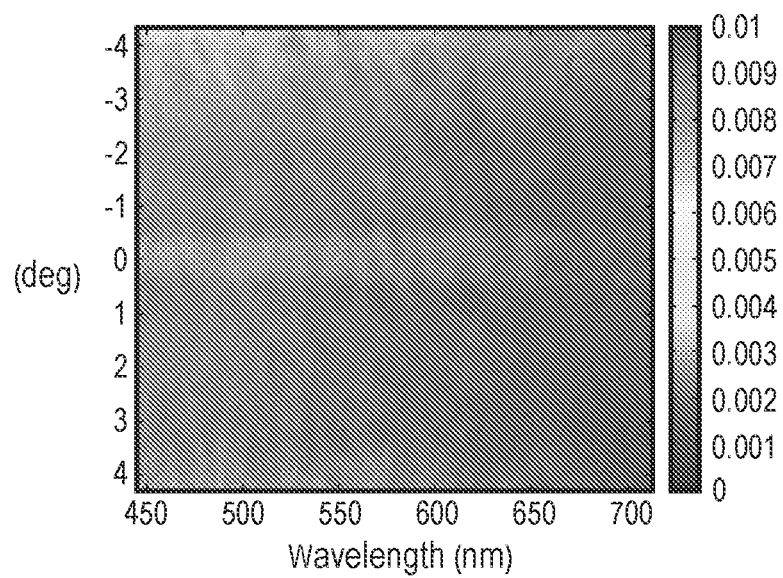
FIG. 3C show a differential light scattering map of the silk film after 4 days of mineralization.
Figure 3D:
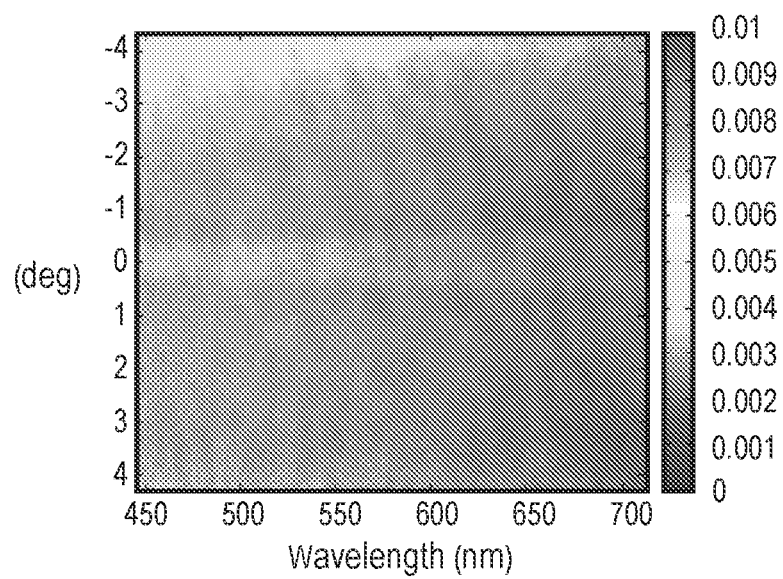
FIG. 3D shows a differential light scattering map of the silk film after 8 days of mineralization.
Figure 3E:
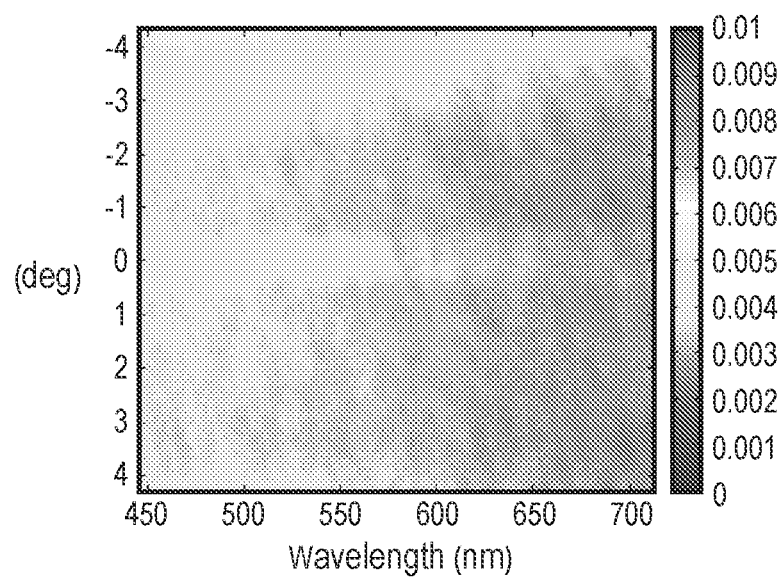
FIG. 3E shows a differential light scattering map of the silk film after 12 days of mineralization.
Figure 3F:
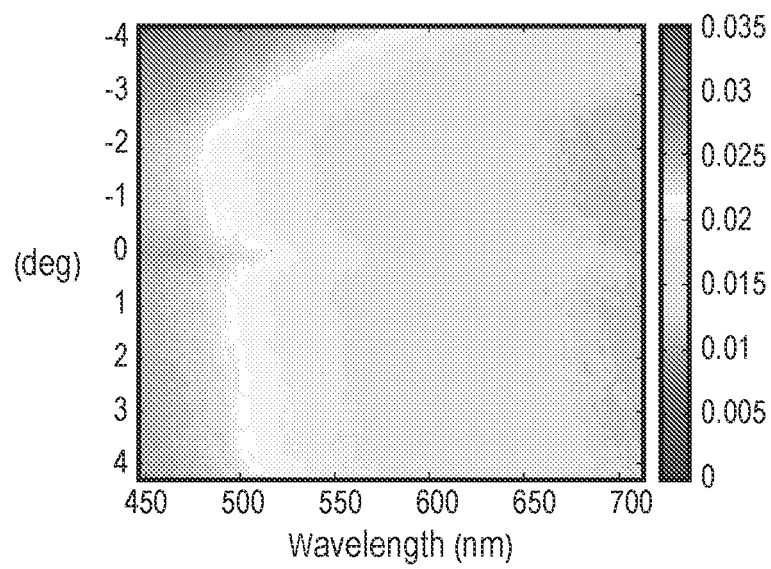
FIG. 3F shows a differential light scattering map of the silk film after 16 days of mineralization.

FIG. 2 schematically depicts an apparatus/system 20 for performing measurements according to the methods of the invention, which includes a broad bandwidth light source 22 (in this case a Xe arc lamp) that generates radiation having a plurality of wavelengths for illuminating a sample 26. In particular, a Xe arc lamp can generate light with wavelengths in a range of about 450 nm to about 700 nm. In general, a variety of broad bandwidth or narrow bandwidth radiation sources can be employed for illuminating the sample. Some examples of such sources include, without limitation, lasers, superluminescent diodes, halogen and quartz lamps.

A lens 21 receives the radiation from the source 22 and provides a collimated beam of radiation that is incident on a mirror 23. The radiation reflected by the mirror 23 passes through a polarizer 24, which linearly polarizes the radiation. The polarized radiation beam passes through a beam splitter 25 to be incident on a surface of the sample 26 under study. In some cases, the sample surface is illuminated at an oblique angle relative to a normal to the surface (e.g., at 45 degrees relative to a vector normal to the surface) so as to avoid the detection of specular reflections.

The radiation backscattered from the sample in response to the illuminating radiation is reflected by the beam splitter 25 toward an analyzer 27. By placing the analyzer parallel and perpendicular to the polarization axis of the illuminating radiation, the backscattered radiation with the respective parallel and perpendicular polarizations can be detected. More specifically, the radiation passing through the analyzer is focused by a lens 28 onto a spectrograph/CCD detector 29. The spectrograph 29 can disperse the incoming backscattered radiation as a function of wavelength, and the CCD detector 29 can detect the dispersed radiation.

While singly scattered photons generally maintain their initial polarization, multiply scattered photons are typically depolarized and can hence include substantially equal amounts of light polarized along the parallel and perpendicular polarizations. Thus, a differential signal corresponding to a difference in intensities of detected backscattered radiation with parallel ($I_{par}$) and perpendicular ($I_{perp}$) polarization ($\Delta I = I_{par} - I_{perp}$) can be used to selectively monitor singly scattered light from the sample.

An analysis module 30 can analyze the detected backscattered radiation, e.g., the aforementioned differential signal, to derive information about mineral constituent(s) of the sample 26. By way of example, the analysis module can include software for operating on the data according to the methods of the invention, such as those discussed above, to derive this information. Such software can be implemented in a variety of ways known in the art including the use of well-known programming languages, such as Java™, Perl, C, C++, to name a few.

As noted above, in some cases the wavelength dependence of the scattered radiation at a plurality of scattering angles can be analyzed to obtain information regarding mineral constituent(s) of a sample. A variety of optical systems can be used to gather wavelength dependent scattering data at a plurality of scattering angles. For example, an article entitled "Simultaneous measurement of angular and spectral properties of light scattering for characterization of tissue microarchitecture and its alteration in early precancer," published in IEEE J Selected Topics Quantum Electron 2003; 9: 243-256 by Kim et al., which is herein incorporated by reference, describes such a system. The system described in FIG. 2 is also capable of acquiring scattered radiation data at multiple angles. Specifically, the incident radiation can be collimated to within a fraction of a degree by a combination of lenses and a pinhole (represented by 21) prior to its incidence on the sample. The spectrograph can be positioned at the Fourier plane of lens 28 so that the light collected at each distinct row of camera pixels in the vertical direction represents light backscattered at a distinct scattering angle. Alternatively, a bandpass filter could be positioned immediately following the polarizer 24 and a CCD camera could replace the spectrograph/CCD assembly. In that case, each pixel on the CCD camera would collect the light backscattered at a distinct angle for the wavelength range transmitted through the bandpass filter.

In some cases, the measurements methods of the invention can be utilized to monitor a mineralization process as a function of time. For example, the light scattering methods discussed above can be employed in different temporal intervals to obtain a "snap shot" of the mineralization process by deriving information regarding the morphology and/or amount of the mineral deposits. The temporal evolution of the mineralization process can then be monitored via the information obtained at different time intervals. For example, in some cases, biominerals exhibit nanoscale crystal morphologies at early stages of formation. The orientation, size and shape of the crystals can vary at different stages of mineralization, i.e., as the mineralization progresses. Hence, in some applications, the measurement methods of the invention can be utilized to obtain a better understanding of the mineralization process and crystal formation in biocomposite materials, which can in turn facilitate the engineering of high performance materials.

In some applications, the methods and systems of the invention can be employed to obtain information regarding the growth of engineered bone tissue including, without limitation, the degree of mineralization, and shape and size of the mineral particles. Biomaterial scaffolds can be used as three-dimensional extracellular matrices to engineer bone tissue and bone implants. The methods and systems of the invention can be utilized to obtain information regarding formation of mineral deposits on such scaffolds (e.g., organic scaffolds). Among the existing scaffolding materials used in tissue engineer, silk is one of the most promising scaffolding materials due to its biocompatibility and favorable mechanical properties. In particular, silkworm silk protein, fibroin, is a natural bioactive polymer with high mechanical strength and elasticity. The fibroin protein is a promising molecule for a number of biomedical and tissue engineering applications due to its biocompatibility, including its use as a scaffolding material in bone tissue engineering.

In the case of biomineralization, organic scaffold matrices control the nucleation and growth of the inorganic mineral structures through acidic protein molecules that provide nucleation sites and dictate crystal orientation and crystal morphology. To understand the mineralization process and to mimic chemical composition and structure of hydroxyapatite found in human body, simulated body fluid (SBF), which has similar ion concentrations as found in blood plasma, can be utilized for ex-vivo mineralization studies. The quality of the bone can depend on bone mineral density, architecture and mineral quality. As noted above, the methods and systems of the invention can be employed to obtain information regarding the degree of mineralization, shape and size of mineral particles of engineered bone tissue, which can in turn provide information regarding the functional and mechanical properties of the engineered bone.

The methods and systems of the invention for deriving information regarding mineralization, such as characterizing density, distribution and morphology of mineral deposits on underlying scaffolds, provide advantages over conventional analytical tools for characterizing mineralization, such as scanning electron microscopy (SEM), x-ray photoelectron spectroscopy (XPS), transmission electron microscopy (TEM), and x-ray photoelectron spectroscopy (XPS). For example, while these conventional tools can destroy a sample under study, the methods of the invention can be utilized non-invasively to dynamically monitor the mineralization process. Moreover, many conventional techniques are not particularly suited for characterizing early stages of mineralization. In contrast, many embodiments of the methods and systems of the invention can be employed to characterize early stages of mineralization.

By way of further illustration of various aspects of the invention, the following Examples are provided. It should be understood that the Examples are provided only for illustrative purposes and are not intended to necessarily indicate optimal results that can be obtained by practicing the measurement methods according to the teachings of the invention.

EXAMPLES

The Examples demonstrate exemplary uses of the present invention. As shown, LSS can be used to assess the progression of mineralization in three different types of silk films (water annealed, methanol treated and poly aspartic acid (PAA) mixed) exhibiting different levels of crystallinity. To gain a better understanding of the origins of the LSS signals, LSS analysis results were compared with standard thermal techniques and SEM. Additional Examples are provided to show the use of the methods and systems of the invention for determining quantitative and morphological changes in simulated body fluid mineralization. LSS can serve as a useful non-invasive tool to assess not only the amount, but also the organization of mineral deposits. Further, it is a technique that can be used at early stages of mineralization, offering early insight in dynamic processes at organic-inorganic interfaces. As such, the methods of the invention offer a novel approach that can improve monitoring, understanding and control of biomineralization.

Example 1

Materials and Methods

1. Preparation of Simulated Body Fluid

In this Example, modified simulated body fluid (m-SBF) was used, which has been proposed for bone-like apatite production. The details of production of the m-SBF can be found in an article entitled "Preparation and Assessment of Revised Simulated Body Fluids" by Oyane et al. published in J. Biomed. Mater. Res. A 65, 188-189 (2003), which is herein incorporated by reference. The chemicals were supplied by Sigma Aldrich, U.S.A. A buffer agent, HEPES (2-[4-(2-hydroxyethyl)-1-piperazinyl] ethanesulphonic acid) and its counter aqueous 1.0 M NaOH were used to keep the pH of the SBF constant. The prepared SBF was filtered through a sterile vented filter unit (Sterivex™—GP, Millipore Co., Bedford, Mass.), which included a polyether sulphone membrane with a pore size of 0.22 microns (μm).

2. Silk Film Preparation

To remove sericin and extract fibroin, *Bombyx mori* silkworm cocoons were boiled for about 30 minutes in an aqueous solution of 0.02 M $Na_2CO_3$ and subsequently rinsed thoroughly with water. The extracted fibroin silk was then dissolved in 9.3 M LiBr solution at 60° C., yielding a 20% (w/v) solution. To remove LiBr, this solution was dialyzed in water, using Slide-a-Lyzer dialysis cassettes (Pierce, MWCO 3500). The final concentration of fibroin silk solution was approximately 8% and fibroin silk films were cast by pouring the acqueous silk fibroin solution into polystyrene petri dishes and allowing them to dry at ambient temperature in a hood for 48 hours. To increase the β sheet content regenerated fibroin films were kept in a water-filled vacuumed (less than about $10^{-3}$ mmHg) desiccator for approximately 24 hours. For the SBF mineralization experiment, films were kept standing against the walls of 1×1×5 $cm^3$ cuvette in m-SBF solution for 16 days and the solution was changed everyday to keep the ion concentration constant.

3. Light Scattering Spectroscopy

The LSS system used in this study was similar to that shown in FIG. 2 above. Briefly, a collimated and linearly polarized light beam from a 500 Watt Xenon lamp in the wavelength region from 450-700 nm was used for illuminating the sample at about 45 from the surface normal in order to avoid specular reflections. The set-up acquired the scattering angle and wavelength dependent intensity of light scattered in the backward direction. The backscattered light was detected through an analyzer that was placed either parallel ($I_{par}$) or perpendicular ($I_{perp}$) to the polarizer. Backscattered intensity maps were acquired from silk films and background, at scattering angles between about −4.2 and +4.2°. The acquisition time for each scattering map was 30 s. To account for the angular and spectral effects in the measurements, induced by the lamp properties, the transmission of the optical components, the spectrograph grating characteristics and the camera quantum efficiency, the background subtracted data was normalized using scattering map of a 99% reflectance standard (LabSphere), which is diffuse surface that reflects approximately 99% of incident light in the wavelength region 400-750 nm without any wavelength dependence. Mostly, singly scattered photons maintain their initial polarization, while multiply scattered photons are depolarized and can include equal amounts of light polarized along the parallel and perpendicular polarizations. Thus, the differential signal, $\Delta I = I_{par} - I_{perp}$ can be used to select only singly scattered light from a specimen.

4. SEM Imaging of Mineralized Silk Films

To observe the morphological variations of deposited minerals, SEM images of silk films were also taken before mineralization, after 1st, 4th, 8th, 12th and 16th days. The silk films were coated with gold and examined using a Zeiss Ultra 55 Field Emission Gun SEM (Carl Zeiss NTS GmbH, Oberkochen, Germany) at 2 kV to assess the morphology of mineral deposits on the films. SEM images were taken at various magnifications to estimate the amount of mineralization. In order to characterize the mineral organization as shown in high resolution SEM images, the radial power spectral density was calculated. Specifically, radial power spectral density $\Phi(\kappa)$ of the image is the square of the magnitude of the Fourier transform of the spatial frequency. The calculated PSD function shows a power law behaviour, $\Phi(\kappa) \propto \kappa^{-\delta}$, in high spatial frequency region, indicative of self affine fractal surface.

5. Experimental Results

Figure 4:
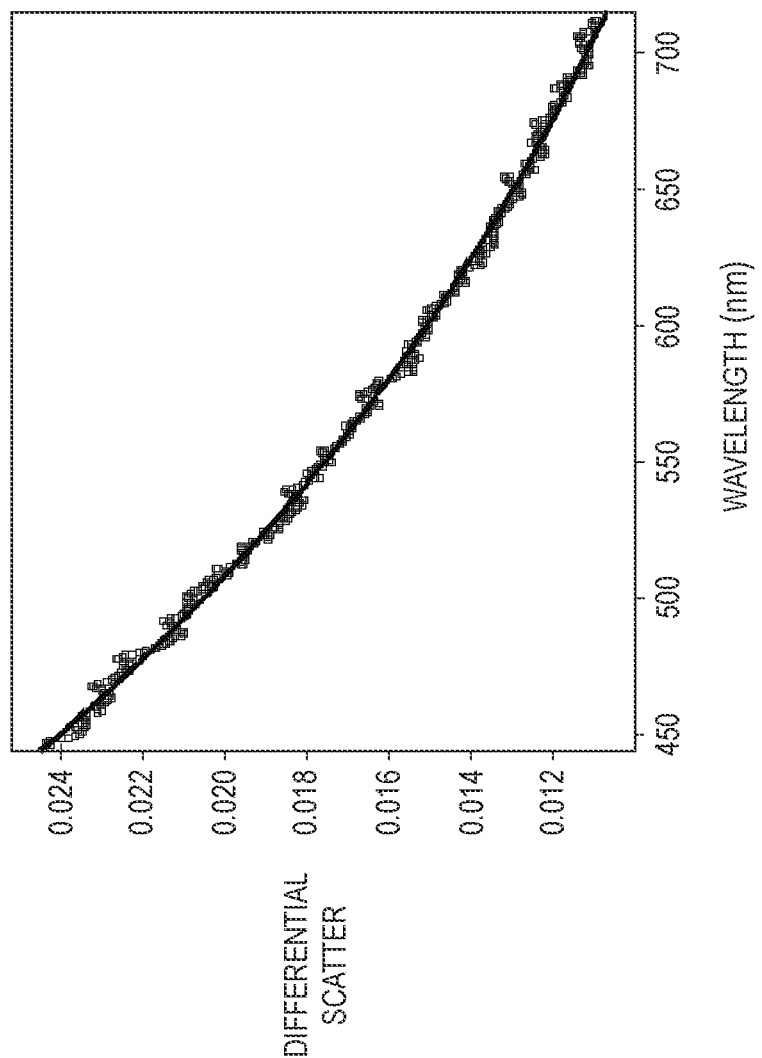
FIG. 4 shows a fit of the differential light scattering data obtained from the silk film after 16 days of mineralization to a fractal model.

FIG. 3A-3F show the differential ($\Delta I$) light scattering maps of silk films prior to the onset of mineralization (day 0), and on the $2^{nd}$, $4^{th}$, $8^{th}$, $12^{th}$ and $16^{th}$ day of mineralization. The differential light scattering signal represents the singly scattered photons and possesses the morphological information of uppermost layer of minerals. The differential light scattering maps were found to be different at each day of mineralization, which suggests a continuous change in the surface topography of the films due to continuous mineral deposition. FIG. 4 shows a fit of the differential light scattering data obtained from the silk film after 16 days of mineralization to a fractal model.

Figure 5A:
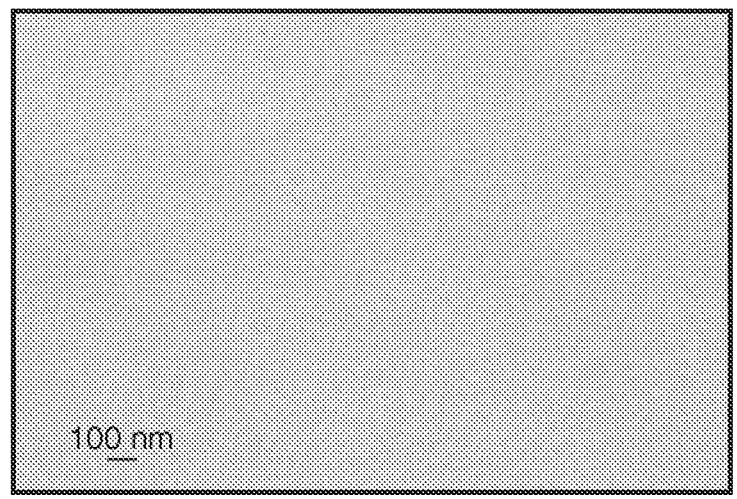
FIG. 5A shows a 100,000× resolution SEM image of a silk film before mineralization.
Figure 5B:
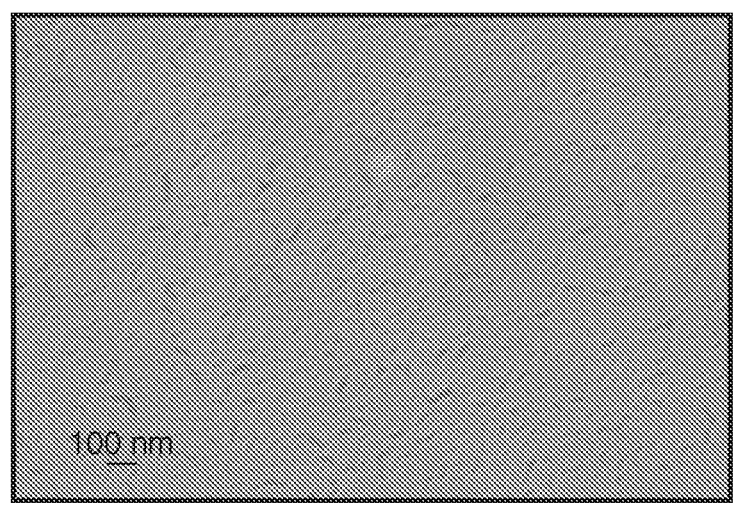
FIG. 5B shows a 100,000× resolution SEM image of the silk film after 2 days of mineralization.
Figure 5C:
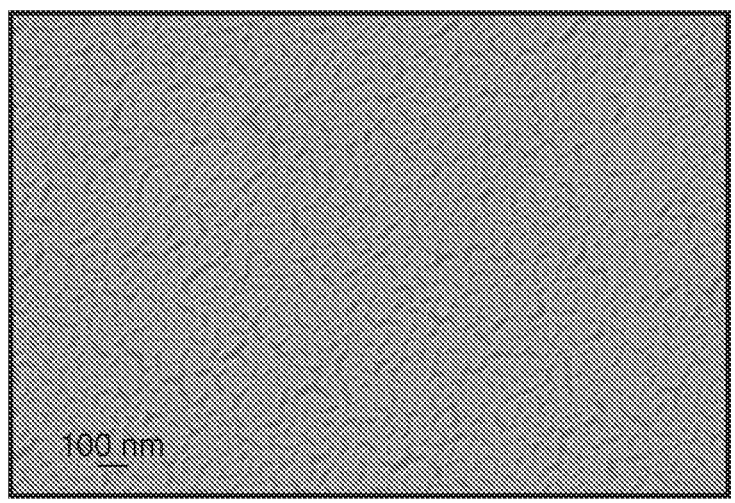
FIG. 5C shows a 100,000× resolution SEM image of the silk film after 4 days of mineralization.
Figure 5D:
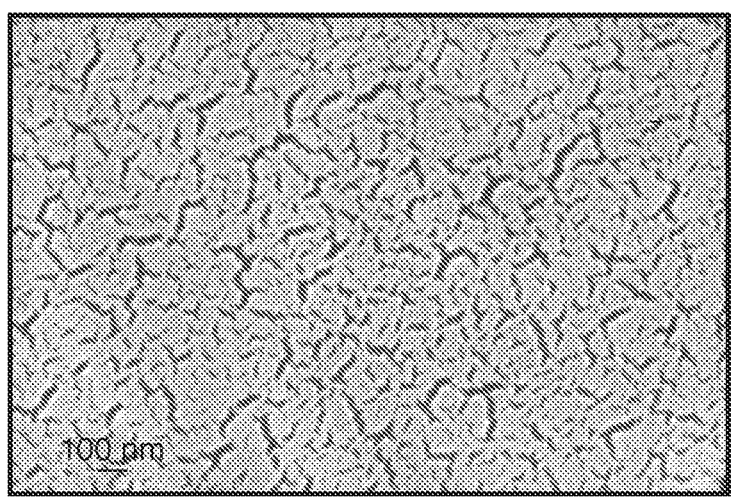
FIG. 5D shows a 100,000× resolution SEM image of the silk film after 8 days of mineralization.
Figure 5E:
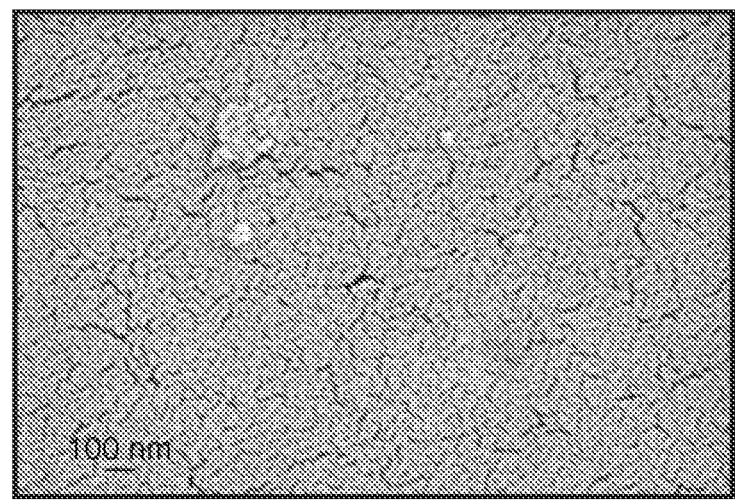
FIG. 5E shows a 100,000× resolution SEM image of the silk film after 12 days of mineralization.

To further confirm the findings of LSS, SEM images were taken of the films. The high resolution (100,000×) SEM images display a consistent variation in the topography of the mineral deposits, as shown in FIGS. 5A-5F. FIG. 6 shows a power law fit to power spectral density (PSD) of the SEM image of the silk film after 16 days of mineralization. These results confirm that LSS methods and systems in accordance with the teachings of the invention can be utilized to detect the nano-scale changes in the surface of mineral deposits at different time points, which can only be seen through high resolution SEM images. The high resolution (eg 100,000×) SEM imaging is, however, not typically suitable technique for studying biological specimens. In particular, there is high possibility that SEM imaging would destroy the biological sample during the measurements due to tightly focused high energy electrons.

Figure 7A:
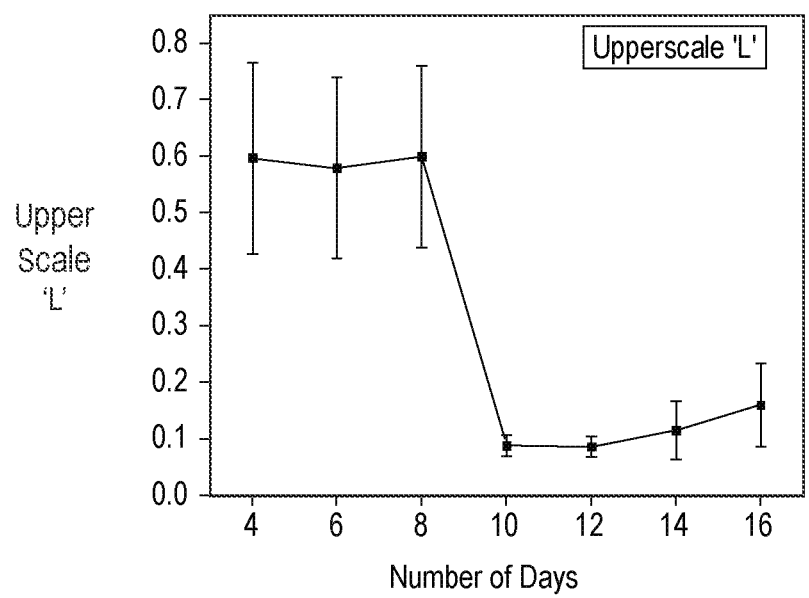
FIG. 7A shows upper scale value L for a mineralized silk film from the $4^{th}$ day of mineralization until $16^{th}$ day of mineralization.

The total light scattering signal ($I_{par}+I_{perp}$) is found to be more sensitive to the degree of mineral deposition on silk films, so it can provide the quantitative information of mineral deposits. In FIG. 7C, an increasing trend in total scattering intensity is observed from before mineralization to $16^{th}$ day of mineralization, which confirms that mineral deposition is increasing with mineralization duration.

To extract the morphological information of deposited minerals, differential LSS spectra at θ=1° were analyzed. To analyze the differential (i.e. $\Delta I(\lambda)$) wavelength-dependent LSS data, a model based on self-affine fractal morphology of the scatterers was used. According to the self-affine fractal model, the wavelength dependence of the singly scattered light is described by the above expression of Equation(2), which is reproduced below:

$$\Delta I(\lambda) \propto \lambda^{-4} \frac{1}{[1+(4\pi L/\lambda)^2]^\alpha}$$

where, the exponent α is related to the Hurst parameter via $H=\alpha-D_E/2$, with $D_E$ the Euclidian dimension of the scattering system and L is the fractal upper scale (the upper bound of fractal correlation lengths). As noted above, the Hurst parameter provides a measure of the roughness of a self affine fractal surface and is limited within the range 0<H<1. The self affine fractal light scattering model is valid under the Born approximation, which applies to weakly scattering systems. As the hydroxyapatite has a high refractive index (n~1.6), the above equation is expected to hold for the topmost layer (few hundred nanometers) of the mineralized films, for which the optical path of scattered light is small despite the high refractive index of the hydroxyapatite layer on the surface of films.

Significant differences were found in the wavelength-dependence of the LSS spectra acquired from SBF mineralized films at different days. To quantitatively explain these differences, the above equation describing light scattering from a self affine assembly of scatterers was fit to the spectra.

Figure 7B:
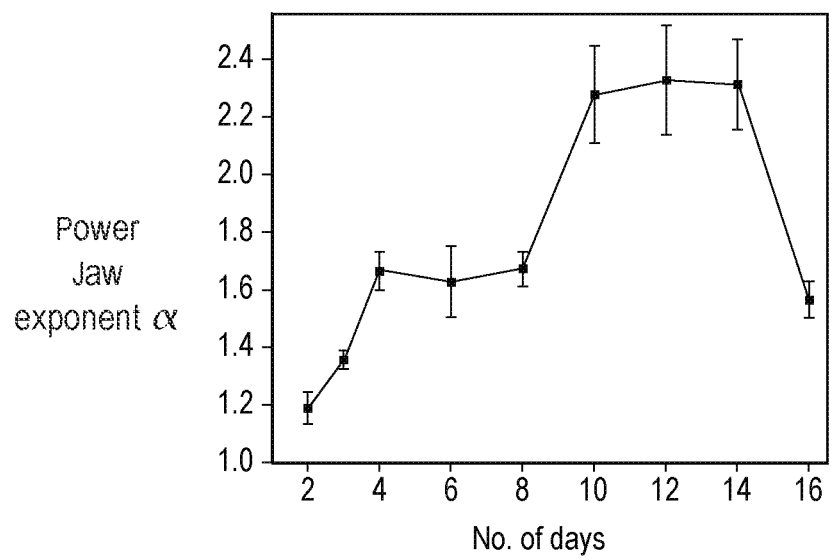
FIG. 7B shows the power law exponent α of a mineralized silk film after the second day of mineralization until the $16^{th}$ day of mineralization.
Figure 7C:
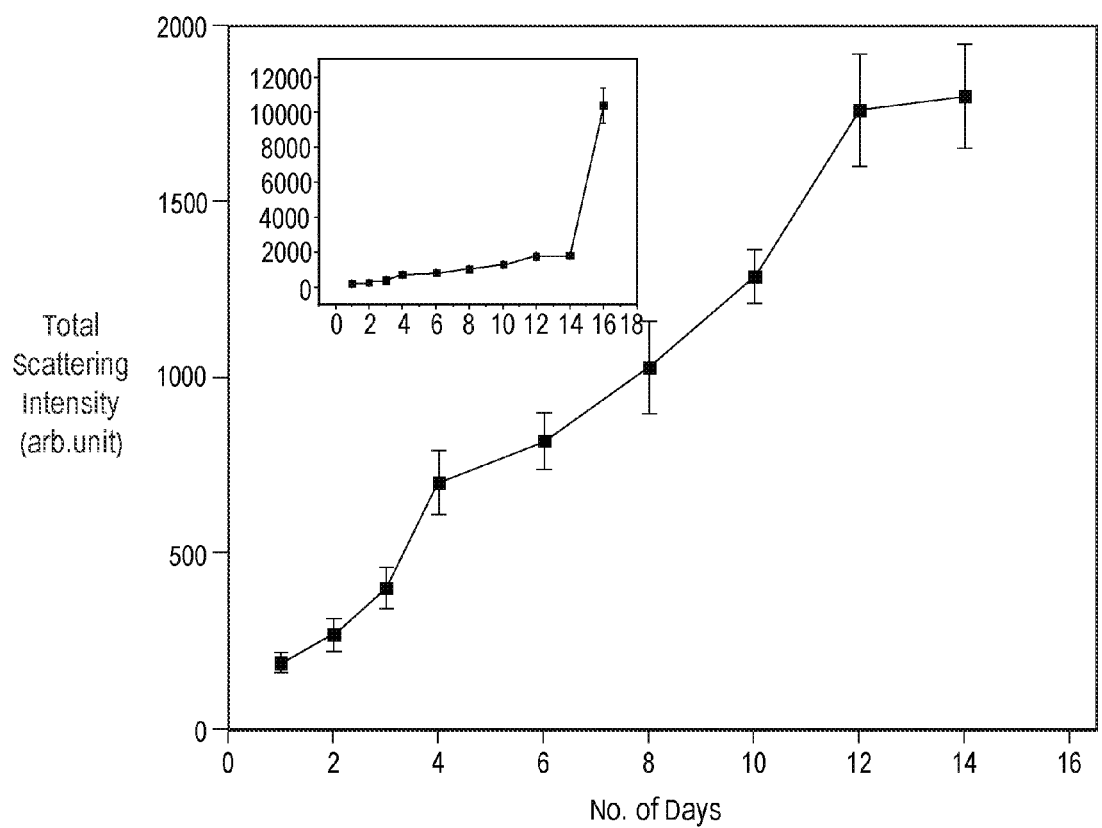
FIG. 7C shows the total scattering intensity variation of different mineralized silk films from before mineralization until $16^{th}$ day of mineralization.

FIG. 7B summarizes the self-affine fractal parameter α obtained from analysis of the LSS spectra of the mineralized films. As mentioned earlier, the power law exponent α contains information about the fractal organization parameter, H, and the dominant scatterer topology, $D_E$. The allowed values of α for each Euclidean dimension are $0.5<\alpha<1.5$ ($D_E=1$), $1<\alpha<2$ ($D_E=2$) and $1.5<\alpha<2.5$ ($D_E=3$). The measured average values of α could imply either a sheet-like (flaky) topology of the films ($D_E=2$), or a bulk, space-filling morphology ($D_E=3$). High magnification (100,000×) SEM images show these films to include an agglomeration of sheet-like mineral deposits on $2^{nd}$, $4^{th}$ and $8^{th}$ day of mineralization, thereby establishing their Euclidean dimension as $D_E=2$. In the case of $12^{th}$ and $16^{th}$ day, SEM images show indicate a three dimensional space filling bead like structures, so Euclidian dimension can be considered to be 3 for these two days. These results indicate that mineralization is a stepwise growth process.

In FIG. 7B, the power law exponent α displays increasing value trend with two segments of constant values up to $14^{th}$ day. After day 14, a sudden decrease was observed in the α value. This variable trend of α might explain the mineral deposition mechanism on the silk film surface as seen in the SEM images. The increasing values of α represent a surface topography transition from a negatively correlated surface (H=0.19, for day 2) to a positively correlated surface morphology (H=0.7, for day 14). The value of Hurst parameter for totally random surface is 0.5.

Figure 5F:
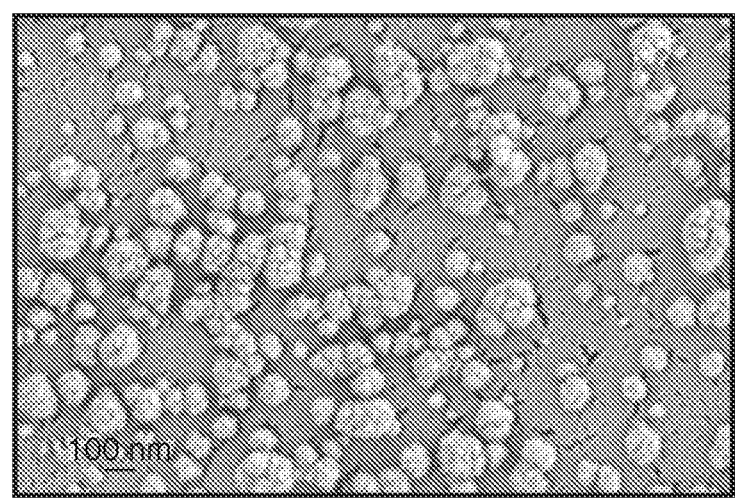
FIG. 5F shows a 100,000× resolution SEM image of the silk film after 16 days of mineralization.
Figure 6:
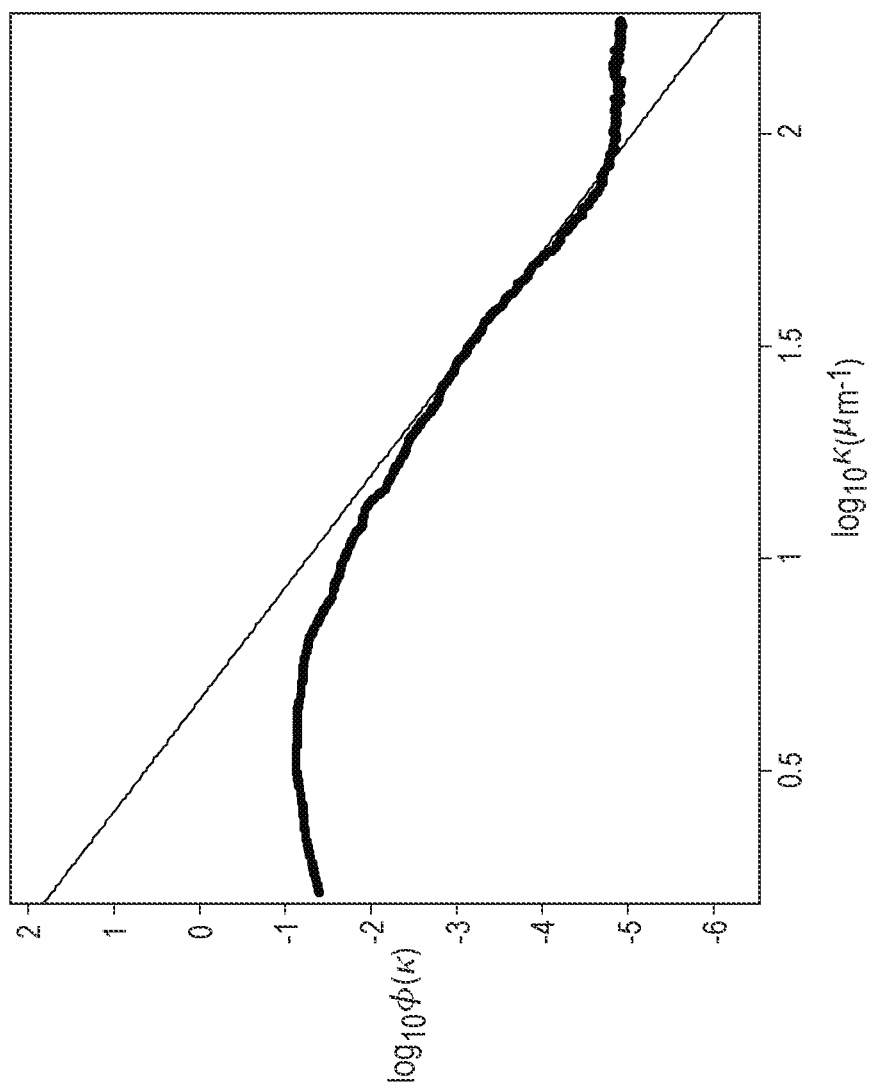
FIG. 6 shows a power law fit to power spectral density (PSD) of the SEM image of the silk film after 16 days of mineralization.

The sudden decrease in α on the $16^{th}$ day could be due to a drastic change in the surface morphology; this change is shown in the $16^{th}$ day SEM image of the film also (FIG. 5F). On the $16^{th}$ day, the Hurst parameter was found to be 0.07, indicating a negatively correlated surface morphology.

FIG. 7A shows the variation of upper scale value L for the mineralized silk films with duration of mineralization. The upper scale value shows a decrease from day 8 to day 12 and a similar change is observed in the SEM images (FIGS. 5D and 5E). The sixteenth day upper scale value of about 170 nm matches closely with the average size of mineral beads in the SEM images. The results further confirm the sensitivity of the LSS techniques according to the invention for detecting nano-scale changes in mineral morphology.

The SBF mineralization of biomaterials is much slower in comparison with some alternate dipping methods, as confirmed by concurrent plots of sixteenth day total intensity information along with TGA-LLS correlation curve obtained for SBF and some alternate dipping methods.

Figure 9:
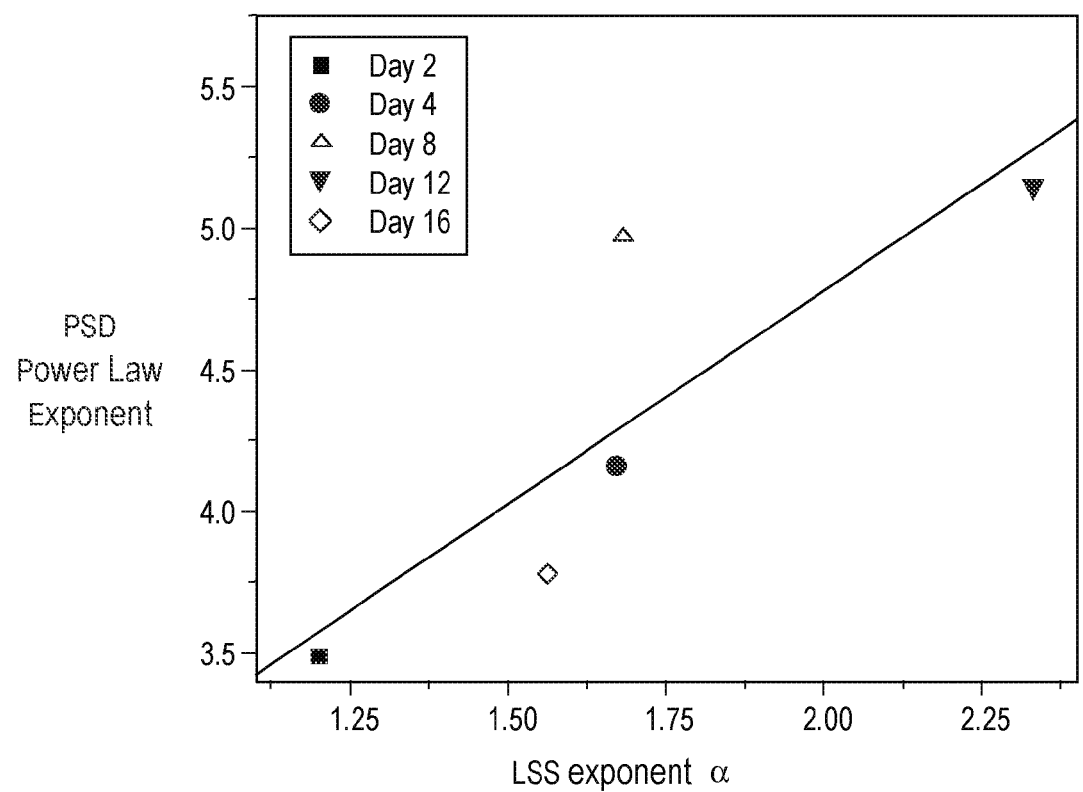
FIG. 9 shows correlation of light scattering exponent α and PSD inverse power law exponent for mineralized silk films at different days of mineralization.

To further confirm the mineral organization, radial power spectral density (PSD) of 100,000× SEM images was calculated. The power spectral density of SEM images displays a power law nature at high frequency region which is indicative of scale invariant self affine fractal organization. The power exponent δ of PSD and power law exponent α of LSS are related as $\alpha=\delta/2-1+De[r]$, which is a linear curve. FIG. 9 shows the relationship between α and δ from day two to day sixteen, it is noteworthy that LSS exponent α and PSD inverse power law exponent δ are qualitatively in line with the above mentioned relationship confirming the self affine fractal morphology of minerals, but quantitatively are slightly different. This quantitative difference in the relationship could be due to multiple reasons. One of those reasons could be that LSS model used is valid for weak scatterers but the refractive index of HA is approximately 1.62, so the assumption of weak scattering may no longer be valid in this case.

The above results demonstrate the feasibility of utilizing LSS as a non-invasive tool for quantitative and organizational assessment of early and continuous mineral deposition on silk films by SBF. Total light scattering intensity, which can be sensitive to the degree of mineralization, can be employed to detect mineral growth as early as second day of mineralization. The power law exponent of the LSS measurements can provide information about the dynamics of mineral deposit topography. In the above study, the Hurst parameter, H, shows a growing positively correlated surface from day two to day 14. The positively correlated variation in the surface morphology suggests evenly deposited minerals on the silk film. A sudden drop in the value of 'α' on day 16, indicates a significant change in the surface topography and SEM images also display a distinct three dimensional bead like mineral agglomeration. The power law nature of PSD function also confirms the self affine morphology suggested by LSS measurements.

Example 2

Materials and Methods

1. Silk Film Preparation

To extract the silk fibroin protein, *Bombyx mori* silkworm cocoons were boiled for 30 minutes in an aqueous solution of 0.02 M $Na_2CO_3$ and rinsed thoroughly with water to extract the glue-like sericin proteins. The extracted silk was then dissolved in 9.3 M LiBr solution at 60° C., yielding a 20% (w/v) solution. This solution was dialyzed in water using Slide-a-Lyzer dialysis cassettes (Pierce, MWCO 3500). The final concentration of aqueous fibroin solution was 8.0% w/v, which was determined by weighing the remaining solid after drying. Pure silk films were cast by pouring the silk fibroin solution into polystyrene petri dishes and allowing it to dry at ambient temperature in a hood for 2 days. To increase the β sheet content, the films were kept in a water-filled vacuumed (less than $10^{-3}$ mmHg) desiccator for approximately 24 hours (water-annealed). To further induce β sheet content some films were also immersed in a 90% methanol solution for about 10 hours (methanol-treated). Polyaspartic acid (PAA) films were prepared by adding 0.2% PAA in the aqueous fibroin solution (PAA-mixed). The thickness of all films was approximately 90±5 μm as assessed using a Leica DMIRE2 microscope equipped with a spectral confocal TCS SP2 scanner (Wetzlar, Germany).

For each mineralization cycle the films were kept in a 0.2 M $CaCl_2$ solution for 20 minutes and then allowed to dry at room temperature. Subsequently, the films were moved to a 0.12 M aqueous $Na_2HPO_4$ solution for 20 minutes. Dicalcium phosphate ($CaHPO_4$) mineral deposits were formed on the surface of silk fibroin films after each mineralization cycle. Each film was subject to seven mineralization cycles.

2. Light Scattering Spectroscopy

The LSS system used in this study was similar to that shown in FIG. 2 above, and is described in detail previously in the aforementioned Kim et al. article, though Kim et al. did not use the system for studying mineralization. Briefly, the set-up acquired the scattering angle- and wavelength-dependent intensity of light scattered in the backward direction. Light in the 450-700 nm region from a 500 watt Xenon lamp was collimated and linearly polarized before illuminating the sample at 45° from the surface normal in order to avoid detecting specular reflections.

The backscattered light was detected through an analyzer that was placed either parallel ($I_{par}$) or perpendicular ($I_{perp}$) to the polarizer. Singly scattered photons maintained their initial polarization, while multiply scattered photons are depolarized and consist of equal amounts of light polarized along the parallel and perpendicular polarizations. Thus, the differential signal, $\Delta I = I_{par} - I_{perp}$ can be used to select only singly scattered light from a specimen. Backscattered intensity maps were acquired from silk films and background, at angles between −4.2 to +4.2 degrees. The acquisition time for each scattering map was about 30 seconds. To account for the angular and spectral effects induced by the lamp properties, the transmission of the optical components, the spectrograph grating characteristics and the camera quantum efficiency, scattered intensity maps were also obtained from a 99% reflectance standard obtained from Lab Sphere of NH, U.S.A. Thus, for each polarization, a calibrated intensity matrix was acquired by subtracting the background from the data and dividing with the reflectance standard map. LSS data were acquired from three films of each type included in this study.

To analyze the differential (i.e. $\Delta I(\lambda)$) wavelength-dependent LSS data, a model described in detail previously [Hunter M, Backman V, Popescu G, Kalashnikov M, Boone C W, Wax A, et al. Tissue self-affinity and polarized light scattering in the born approximation: A new model for precancer detection. *Phys Rev Lett* 2006;97: 138102-138105.] assuming self-affine fractal morphology of the scatterers (i.e. mineral deposits) was used. The characteristic property of a fractal object is scale invariance. In the case of a self-similar fractal, the scale invariance is isotropic (an object appears indistinguishable at varying scales), whereas self-affinity implies anisotropic scale invariance i.e., a self-affine fractal function $f(x)$ has a variance, $S(x)=<|f(x+a)-f(x)|^2>$, which scales according to $S(bx) \propto b^H S(x)$, where the Hurst parameter, H, is limited to the range 0<H<1 [Voss R F. Characterization and measurement of random fractals. *Physica Scripta* 1986;T13: 27-32.]. In self-similar fractals, scale invariance often results from a highly organized, iterative generative process (e.g., the progressive branching in fern leaves or human lung architecture). Self-affinity, on the other hand, is associated with random (or quasi-random) processes [Mandelbrot B B. The Fractal Geometry of Nature. Rev ed., 19th printing (W.H. Freeman & Co., New York, 2000).]. Brownian motion, for example, is a self-affine process: the projection of a "drunkard's walk" on any particular spatial axis, as a function of time, is a self-affine function with a value of H=0.5. Fractional values of H smaller than, or greater than, H=0.5 imply varying degrees of persistence (positive correlations), or anti-persistence (negative correlations), superimposed on an underlying random process [Mandelbrot B B. The Fractal Geometry of Nature. Rev ed., 19th printing (W.H. Freeman & Co., New York, 2000).].

Self-affine fractal organization has been observed widely in nature [Mandelbrot B B. The Fractal Geometry of Nature. Rev ed., 19th printing (W.H. Freeman & Co., New York, 2000).], including in CT images of trabecular bone [Dougherty G, Henebry G M. Fractal signature and lacunarity in the measurement of the texture of trabecular bone in clinical CT images. *Med Eng Phys* 2001;23: 369-380]. The self-affine fractal model discussed above (See Equations (1), (2) and (3)) was used to analyze the LSS data. [Dougherty G, Henebry G M. Fractal signature and lacunarity in the measurement of the texture of trabecular bone in clinical CT images. *Med Eng Phys* 2001;23: 369-380]. As noted above, Eqn. (2) above is valid under the Born approximation, which applies to weakly scattering systems [Hunter M, Backman V, Popescu G, Kalashnikov M, Boone C W, Wax A, et al. Tissue self-affinity and polarized light scattering in the born approximation: A new model for precancer detection. *Phys Rev Lett* 2006;97: 138102-138105]. We expect this equation to hold for the topmost layer (few hundred nm) of our mineral films, for which the optical path difference of incident and scattered rays is small despite the high refractive index of the hydroxyapatite films (n~1.6) [Hunter M, Backman V, Popescu G, Kalashnikov M, Boone C W, Wax A, et al. Tissue self-affinity and polarized light scattering in the born approximation: A new model for precancer detection. Phys Rev Lett 2006;97: 138102-138105].

3. Thermal Measurements

To estimate the β sheet content in the three different types of films, temperature modulated differential scanning calorimetry (TMDSC) was used. This technique is known in the art and is described in [Xiao Hu, Kaplan D L, Cebe P. Determining beta-sheet crystallinity in fibrous protein by thermal analysis and infrared spectroscopy. *Macromolecules* 2006;39: 6161-6170]. Specifically, we employed reversing heat capacity curves to determine the heat capacity increment, $\Delta C_p$, at the glass transition temperature, $T_g$, of each film type. The reversing heat capacity in TMDSC represents a heat effect that is reversible within the range of the temperature modulation employed in these measurements. The glass transition temperature is the temperature that defines the change in the physical properties of amorphous materials from a solid-like to a liquid-like phase. Only the mobile fraction of the silk fibroin contributes to the principal glass transition step. Thus, $\Delta C_p$ is directly proportional to the mobile fraction of the silk protein and inversely proportional to the rigid fraction of the protein. It has been shown that over 97% of this rigid fraction consists of crystalline β-sheets and the crystalline fraction of the silk protein, $\varphi_c$, within a sample examined by TMDSC can be related to $\Delta C_p$ using the expression: $\Delta C_p = 0.475 - 0.494 * \varphi_c$ [Xiao Hu, Kaplan D L, Cebe P. Determining beta-sheet crystallinity in fibrous protein by thermal analysis and infrared spectroscopy. Macromolecules 2006;39: 6161-6170.]. Samples with weight of about 5-8 mg were placed into aluminum pans and heated in a TA Instruments 2920 DSC, which was purged with a dry nitrogen gas flow of 30 mL/min. The instrument was calibrated for empty cell baseline and with indium for heat flow and temperature. The samples were heated at 4° C./min from room temperature to ~230° C., i.e. the degradation temperature of the fibroin molecule [Xiao Hu, Kaplan D L, Cebe P. Determining beta-sheet crystallinity in fibrous protein by thermal analysis and infrared spectroscopy. Macromolecules 2006;39: 6161-6170.], with a modulation period of 60 s and temperature amplitude of 0.315° C. To calculate the specific reversing heat capacity increment $\Delta C_p$, a tangent was drawn along the specific reversing heat capacity curve before the glass transition temperature and extrapolated up to 230° C. The perpendicular distance between the heat capacity at 230° C. and this tangent was defined as $\Delta C_p$.

The mineral content in different films was estimated from thermogravimetric measurements (TGA). TGA is used primarily for determining thermal stability of polymers. Besides providing information on thermal stability, TGA may be used to characterize polymers through weight loss of a known entity and the residual weight of the sample. In the case of mineralized silk films the residual weights were correlated with amount of mineralization in each film. TGA measurements were performed using a TA 500Q machine. Samples were heated up to 600° C. with a step of 10° C./min under an inert nitrogen atmosphere.

4. SEM Measurements

A small part of silk film was removed after LSS data acquisition, coated with gold and examined using a LEO Gemini 982 Field Emission Gun SEM (Thornwood, N.Y.) to assess the morphology of mineral deposits on the films. In order to characterize quantitatively the organization of mineral deposits as revealed by 10,000× SEM images, Fourier analysis was used. Specifically, we determined the angularly averaged power spectral density (PSD) as a function of spatial frequency, κ, for each image. Our PSD spectra showed inverse power law behavior at high spectral frequencies, and a consistent tendency to level off (κ-independence) at low values of κ. As described by Schmitt and Kumar [Schmitt J M, Kumar G. Turbulent nature of refractive-index variations in biological tissue. *Opt Lett* 1996;21: 1310-1312], this behavior is characteristic of a self-affine fractal with an upper scale, L, limiting the range of fractal correlations, and can be described by the following equation:

$$\Phi(\kappa) \propto \frac{1}{(1+\kappa^2 L^2)^m} \quad (3)$$

where 1/L is the spatial frequency at which the PSD function transitions from inverse power law, $\Phi(\kappa) \propto \kappa^{-\delta}$, to κ-independence, and the power exponent δ=2 m is related to the Hurst parameter via:

$$H=(\delta-1)/2 \quad (4)$$

Although some of our PSD spectra followed eqn. (3) closely, many exhibited additional low frequency components that deviated from eqn. (3). Quantitative analysis of our SEM images, therefore, was only performed in the inverse power law (fractal) regime at high spatial frequencies, by fitting to a simple inverse power law, $\Phi(\kappa) \propto \kappa^{-\delta}$ over the range 6 μm$^{-1}$<κ<22 μm$^{-1}$. The Hurst parameters thus obtained were compared to those derived via differential LSS (eqn. (2)).

5. Statistical Analysis

To assess the level of significance in the differences of parameters characterizing the different types of films we performed a standard two-tailed t-test [Drezek R, Brookner C, Pavloval Ina, Boiko I, Malpica A, Lotan R, et al. Autofluorescence microscopy of fresh cervical-tissue sections reveals alterations in tissue biochemistry with dysplasia. *Photochem Photobiol* 72001;3: 636-641]. The reported correlation coefficients were calculated using a built-in Matlab function.

Example 3

Quantitative Assessment of Mineralization in Silk Film Using Light Scattering Spectroscopy Wavelength and scattering-angle dependent light scattering maps were acquired from water annealed, methanol-treated and PAA-mixed silk films prior to and following 1, 3, 5 and 7 mineralization cycles. The sum of the maps acquired along the parallel and perpendicular polarizations relative to the incident light represent the total amount of light backscattered from these films. Water annealed and methanol treated films were almost transparent before mineralization and did not scatter much of the incident light, as evident from the very low intensity of the map (data not shown). A significant growth in scattering intensity was observed after each cycle of mineralization for all types of films (data not shown). This is explicitly shown in FIG. 3, which includes the mean integrated intensity of the light scattered over the entire detected wavelength and angular range from three films of each type.

Example 4

β Sheet Assessment of Silk Films Using TMDSC

The light scattered intensity detected from the PAA-mixed films was significantly higher than that detected from the water annealed and methanol-treated films prior to mineralization (p<0.001). This is consistent with the more hazy appearance of the PAA films, which in turn may be attributed to the higher content of β-sheets. To assess directly the β sheet content of the films included in the study, we performed a series of TMDSC measurements on all types of silk films. The thermal stability of silk filmed varies with the β sheet content, with a higher amount of β sheet leading to a higher thermal stability. As a result, the heat capacity increment $\Delta C_p$ extracted from these measurements as described in the methods section has been shown to correlate highly with the β sheet content of silk films [Xiao Hu, Kaplan D. L., Cebe P. "Determining beta-sheet crystallinity in fibrous protein by thermal analysis and infrared spectroscopy, Macromolecules 2006: 39,: 6161-6170] The specific reversing heat capacity as a function of temperature calculated from these measurements for representative films is shown in FIG. 4A. The reversing heat capacity increment for water annealed, MeOH and PAA films was found to be 0.2092±0.002, 0.20±0.005 and 0.19451±0.009 (J/g-C), respectively, corresponding to crystalline fractions of 53.8%, 55.67% and 56.78% respectively. These measurements indicate that the β sheet content of PAA-mixed films is higher than that of the methanol-treated and water annealed films, which could at least partially explain the higher integrated light scattering levels prior to mineralization for these films.

Example 5

Quantitative Characterization of Mineralization Using TGA and LSS

To determine whether the integrated light scattering intensity of the films following mineralization could be correlated with the level of mineral deposition, we performed TGA measurements of the films at the end of the 7$^{th}$ cycle of mineralization. The TGA thermograms of a representative set of mineralized silk films are shown in FIG. 4B. The PAA mixed film had the highest residual weight and the water annealed films has the least residual weight at 400° C. and above. The difference in the residual weight of the respective films was due to difference in the amount of deposited mineral. The TGA residual weight of each film correlated (correlation coefficient 0.89) with the corresponding integrated light scattering intensity, as shown in FIG. 4C. Therefore, the amount of light backscattered from the films could serve as a non-invasive indicator of the level of mineral deposition. The addition of the PAA provides a significant increase in carboxyl group content, chemistry known to promote nucleation and crystal growth [Li Chunmei, Jin H J, Botsaris G D, Kaplan D L. Silk apatite composites from electrospun fibers. *J Mater Res* 2005; 20:

3374-3384; Kong X D, Cui F Z, Wang X M, Zhang M, Zhang W. Silk fibroin regulated mineralization of hydroxyapatite nanocrystals. *J Crystal Growth* 2004; 270, 197-202.]. The TMDSC and TGA measurements indicate that higher levels of crystallinity yield higher levels of mineralization. This correlation may reflect the more ordered structures in more highly crystalline materials, perhaps inducing more organization for the serine hydroxyl groups present in the crystalline domains, as possible sites of mineral nucleation. Further, the increased beta sheet content may also induce more organization in the less crystalline domains in the silk structures as well, altering location of nucleating groups, such as the aspartic and glutamic acid side chains (~3% of the total amino acids) containing carboxyl groups, further optimizing locations for nucleation and crystal growth.

Example 6

Assessment of Mineral Deposit Organization Using LSS and SEM

LSS was used to characterize the organization of the minerals deposited on the film surface, as they can scatter light due to a difference between their refractive index and that of air and the underlying film. To identify the spectral features of the light that is scattered in the backward direction after undergoing a single scattering event, we subtracted the LSS maps acquired along the parallel and perpendicular directions of polarization relative to that of the incident light. The wavelength dependent features of these residually-polarized LSS spectra, $\Delta I(\lambda)$, at $\theta=1°$ from a representative set of water annealed, methanol-treated and PAA-mixed films prior to and following 1, 3, 5 and 7 mineralization cycles is shown in FIG. 5. We observed that the single scattering intensity of mineralized films decreased with increasing wavelength in a manner consistent with a self-affine fractal morphology of the mineral deposits as described by Eq. 1. FIG. 6 summarizes the self-affine fractal parameters $\alpha$ and L obtained from analysis of the LSS spectra of the different films shown in FIG. 5. Methanol-treated and PAA-mixed films showed similar power exponents ($1.75<\alpha<2.0$) and little sensitivity to the mineralization cycle. Water-annealed films, on the other hand, showed markedly lower power exponents ($0.95<\alpha<1.7$) and a trend towards lower values at higher mineralization cycles. For all films, the fractal upper scale values were constrained to the range 150 nm<L<350 nm, indicating the dominant LSS single-scattering signature was from submicron morphological features of these films.

As discussed above, the exponent $\alpha$ contains information about the fractal organization of a mineral film (Hurst parameter, H) as well as about the dominant film topology ($D_E$). Since H can vary between $0<H<1$, the range of $\alpha$ values allowed for each Euclidean dimension is $0.5<\alpha_1<1.5$, $1.0<\alpha_2<2.0$ and $1.5<\alpha_3<2.5$ for $D_E=1$, 2 and 3, respectively. This suggests that in water-annealed films the dominant film topology contributing to LSS spectra, $\Delta I(\kappa)$, was $D_E=1$ and/or 2, whereas in methanol-treated and PAA-mixed films the dominant single-scattering contributions arose from $D_E=2$ and/or 3 features.

Figure 8:
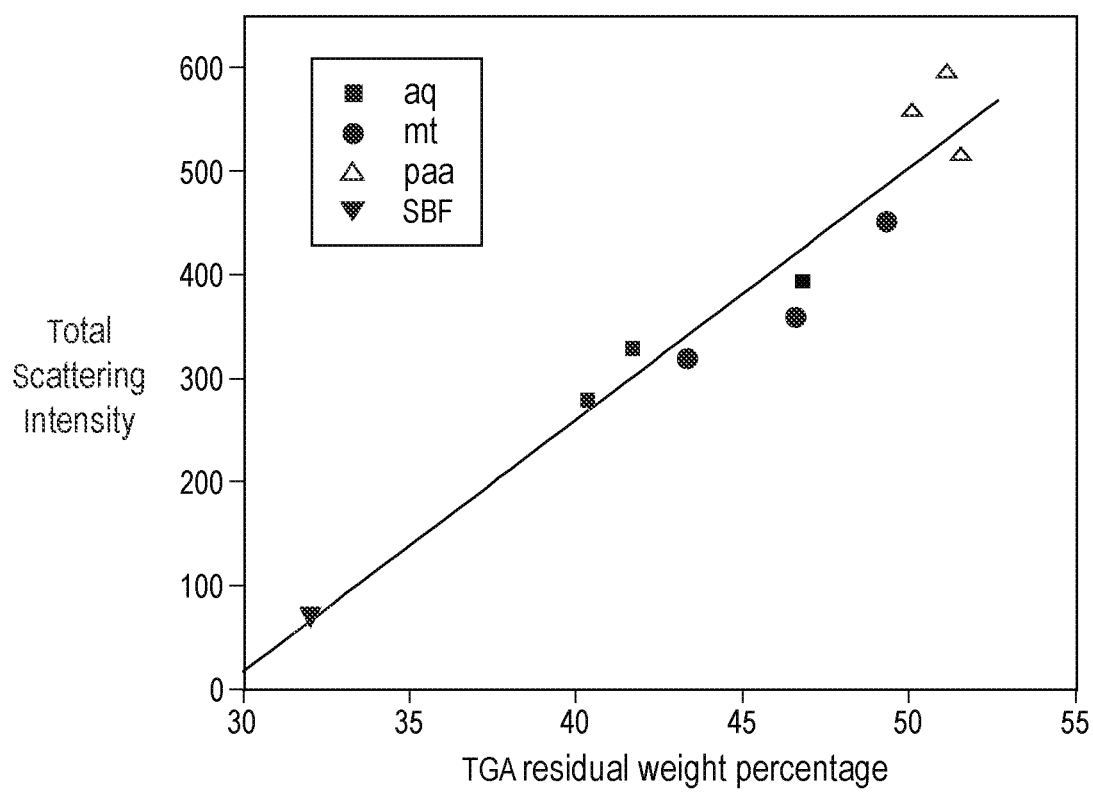
FIG. 8 shows correlation of SBF light scattering signal at $16^{th}$ day of mineralization of a silk film (star) with light scattering and TGA residual weights of mineralized water annealed (square), MeOH treated (circle) and PAA mixed films (triangle)

For the case of water-annealed films, the ambiguity in film topology derived via differential LSS can be removed by visual inspection of the SEM images from these films. A value of $D_E=1$ would imply the dominant surface morphology to be composed of a random (or near-random) network of mineral filaments of submicron diameter and mesh size on the order of L (180-250 nm in water-annealed films). No such features were evident in the SEM images of the water-annealed films (FIG. 7), even at 30,000× magnification (FIG. 8A), thereby ruling out a filamentous fractal film morphology ($D_E=1$). This implies that the differential LSS signal from the water-annealed films is dominated by single scattering from sheet-like fragments or flakes in the mineral surface layer (i.e., $D_E=2$), with flake sizes on the order of L. This interpretation is consistent with the loosely packed, scaled appearance of the SEM images shown in FIGS. 7 and 8A. According to eqn. 2, the measured values $1.75<\alpha<2.0$ in water-annealed films thus indicate a surface film morphology dominated by self-affine, submicron platelets with Hurst parameters in the range $0.75<H<1$ (indicating persistently, or positively, correlated surface height variations, as in typical Earth landscapes [Mandelbrot B B. *The Fractal Geometry of Nature*. Rev ed., 19th printing (W.H. Freeman & Co., New York, 2000); Power W L, Tullis T E. Euclidean and fractal models for the description of rock surface roughness. *J Geophys Res* 1991;96: 415-424])

For methanol-treated and PAA-mixed films it is harder to distinguish between the two possible film topologies, $D_E=2$ and $D_E=3$, in the SEM images (FIGS. 8B and 8C). These mineral films, however, appear far more densely packed than in the water-annealed silk, and it is thus more likely that differential LSS from these films samples bulk ($D_E=3$) sections of their topmost layer, rather than flakes or plates ($D_E=2$). According to eqn. 2, a value of $D_E=3$ would imply the Hurst parameter in these films to vary over the range $0.25<H<0.5$, indicating anti-persistent (or negative) correlations in their 3-dimensional packing or density. This is in sharp contrast to the persistent (positive) correlations inferred for the water-treated films.

To determine whether the fractal parameters extracted from the analysis of the polarized light scattering spectra were indeed representative of the organization of mineral deposits on silk films, we removed a small piece of one set of films after each LSS measurement and imaged it using SEM. A representative set of images acquired from the water annealed films is shown in FIG. 7. To study the nature of the variation in the surface structures of these films, we evaluated the angularly averaged (radial) power spectral density (PSD), $\Phi(\kappa)$, of these images from their two-dimensional Fourier transform [Schmitt J M, Kumar G. Turbulent nature of refractive-index variations in biological tissue. Opt Lett 1996;21: 1310-1312.]. FIG. 9 shows the corresponding angle-averaged (radial) power spectral density (PSD), $\Phi(\kappa)$, curves over a range of spatial frequencies $0.4\ \mu m^{-1}<\kappa<25\ \mu m^{-1}$ of the SEM images shown in FIG. 7. The PSD curves generally exhibit three types of functional dependence on spatial frequency. At high frequencies ($0.8\ \mu m^{-1}<\log_{10}\kappa<1.35\ \mu m^{-1}$), there is a clear inverse power law behavior, $\Phi(\kappa)\propto\kappa^{-\delta}$, with power exponents typically in the range $1<\delta<2$. At intermediate frequencies ($0.5\ \mu m^{-1}<\log_{10}\kappa<0.8\ \mu m^{-1}$), the PSD spectra transition into $\kappa$-independent region, which in some cases persists over the entire low frequency range (e.g, FIG. 8 in $1^{St}$ and $3^{rd}$ cycles of mineralization). In other cases, however, an additional and sometimes structured (oscillatory) component develops at low spatial frequencies ($\log_{10}<0.5\ \mu m^{-1}$).

Figure 10:
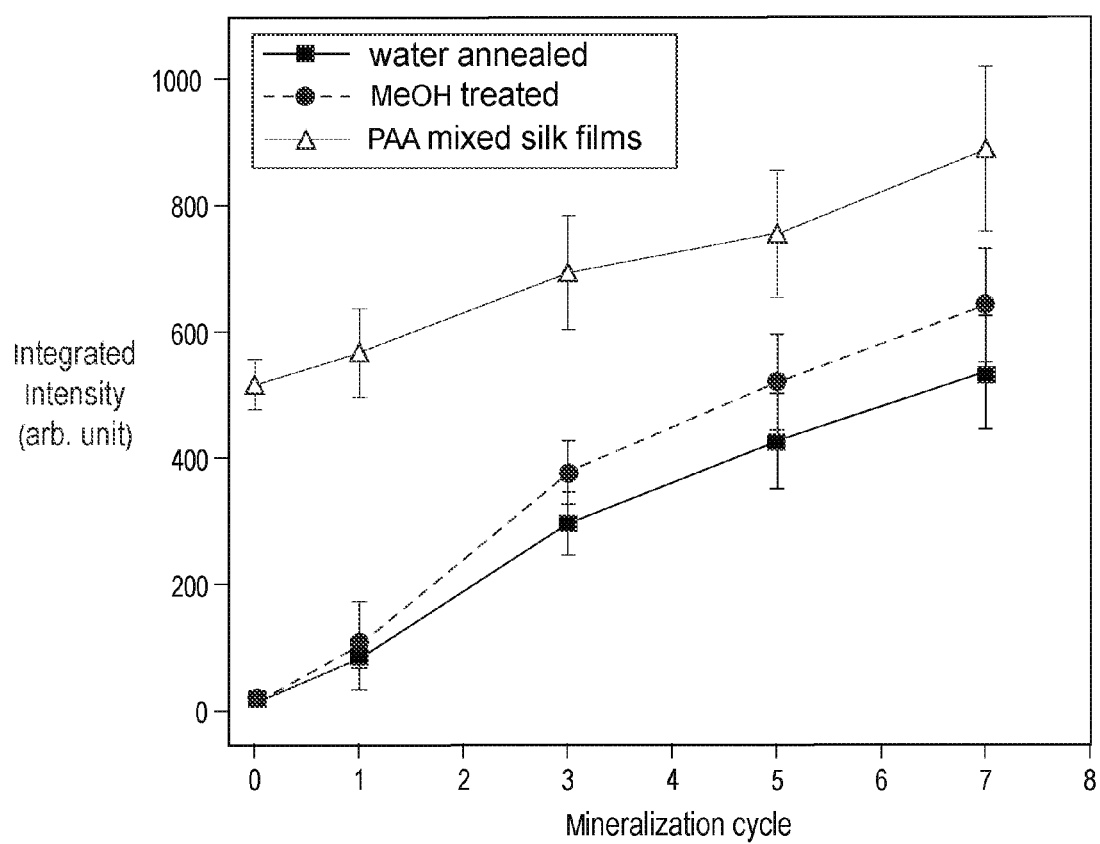
FIG. 10 is a graph of the mean integrated intensity of the light scattered over the entire detected wavelength and angular range from three films of each type: water annealed (■ solid square), MeOH treated (● solid circles) and PAA mixed silk films (▲ solid triangles)
Figure 11A:
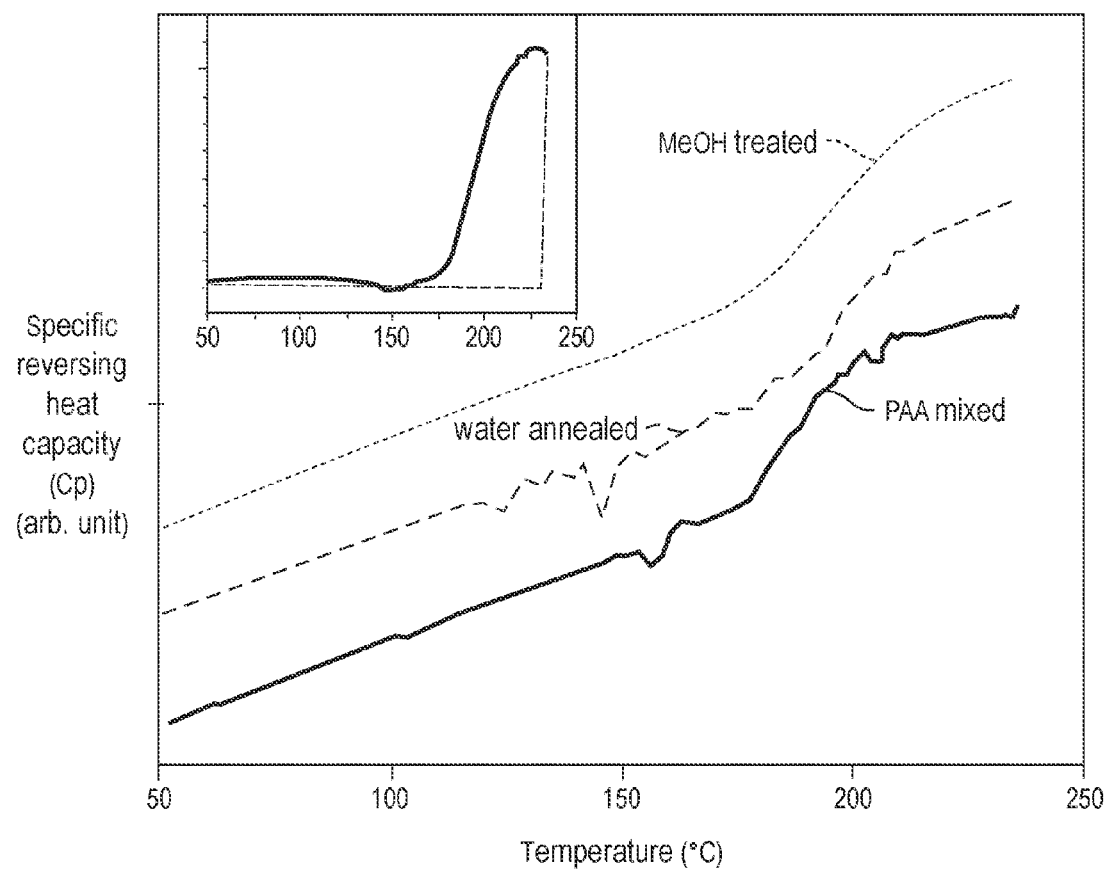
FIG. 11A is a graph of the specific reversing heat capacity $C_p$ of MeOH treated (dot line), water annealed (dash line) and PAA mixed (solid line) films during TMDSC scanning at the heating rate of 4° C./min (Inset shows the method of $\Delta C_p$ calculation for MeOH treated film)
Figure 11B:
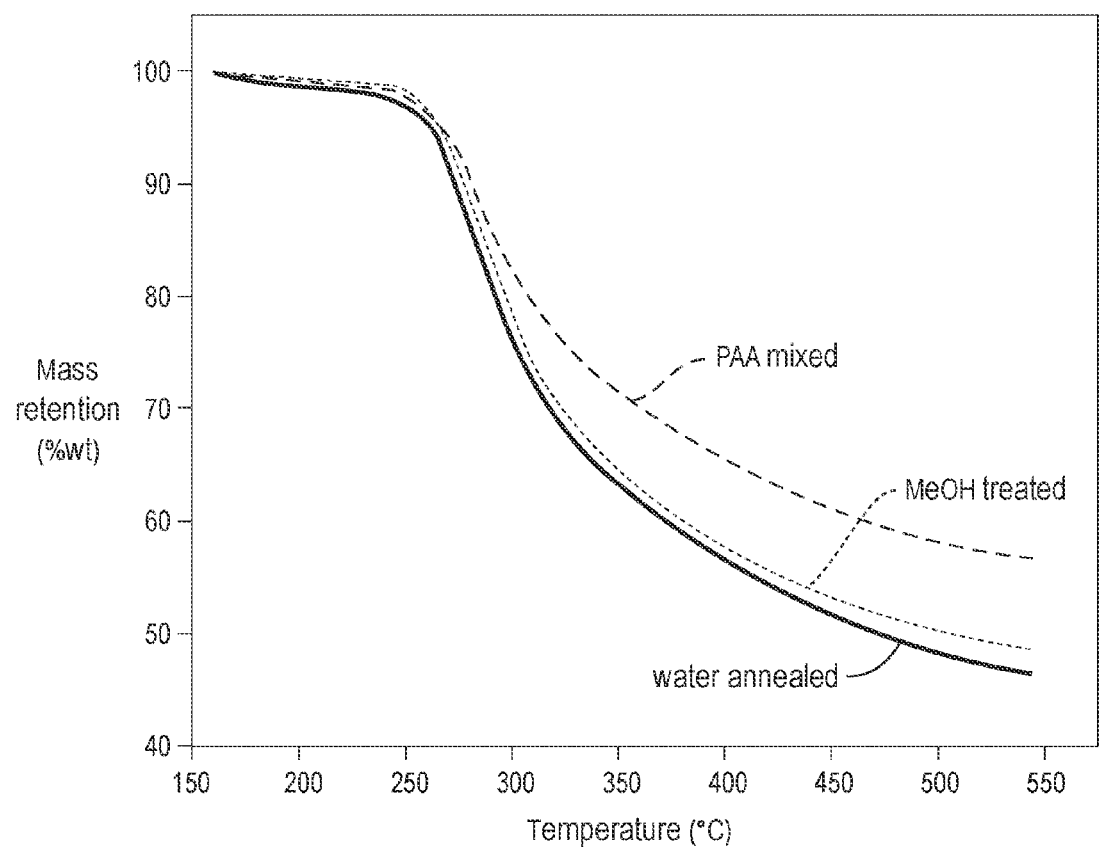
FIG. 11B is a graph of the mass retention versus temperature of TGA thermograms of water annealed (solid line), MeOH treated (dots) and PAA mixed film (dash) after seventh cycle of mineralization showing that PAA mixed films demonstrate highest residual weights at higher temperatures.
Figure 11C:
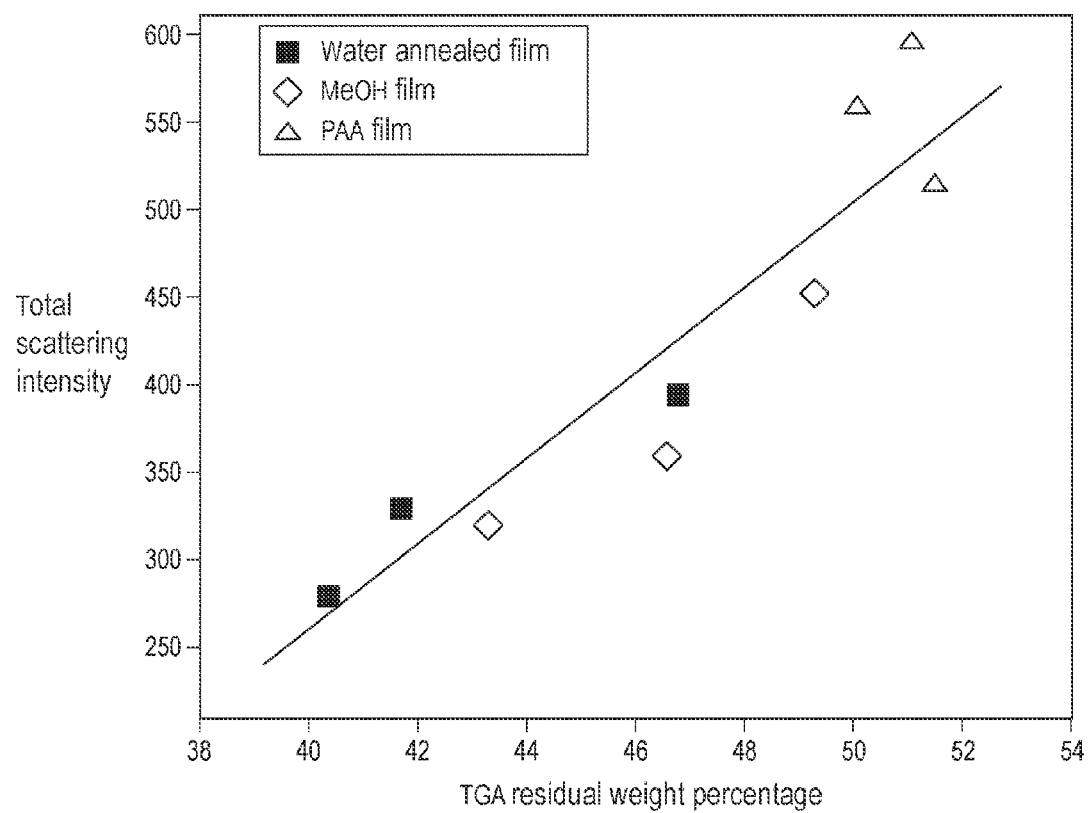
FIG. 11C is a graph of the total scattering intensity versus the TBA residual weight percentage showing the correlation (correlation coefficient of 0.8924) of light scattering intensity and TGA residual weights for water annealed, MeOH treated and PAA mixed silk films.
Figure 12A:
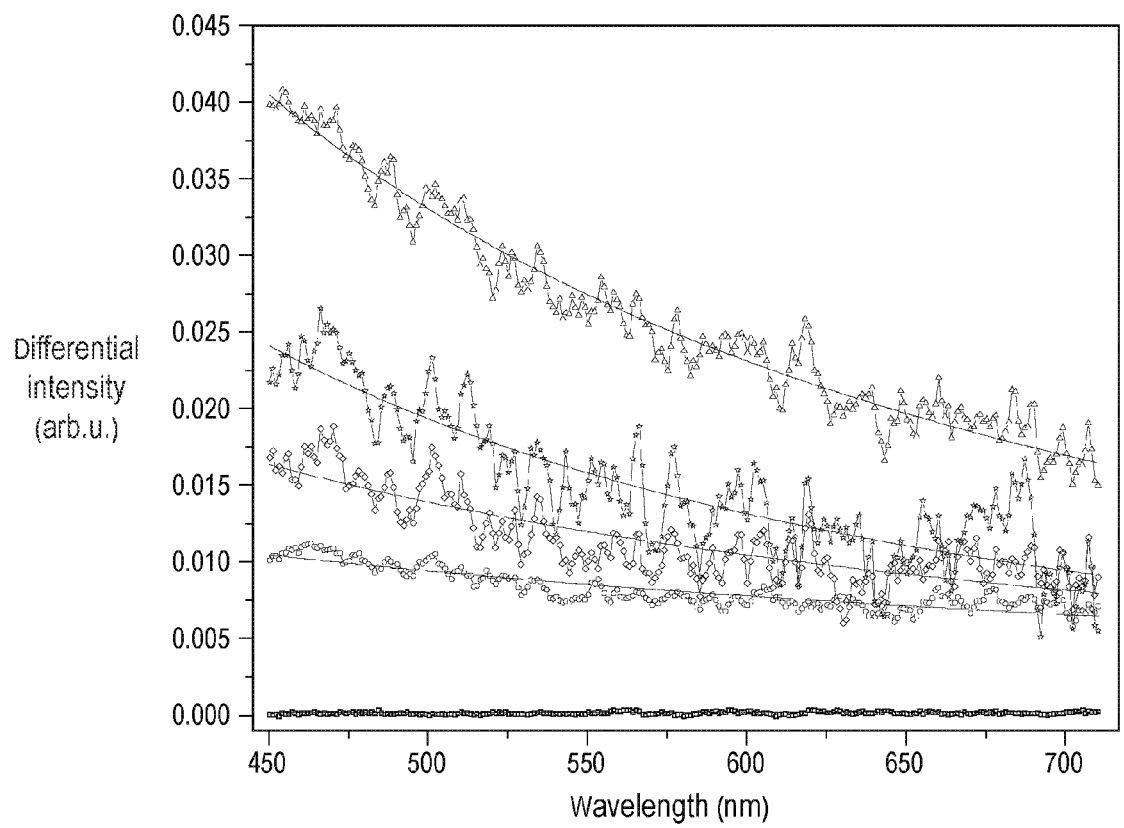
FIG. 12A is a light scattering spectroscopy (LSS) spectra of water annealed films at different cycles of mineralization (solid lines are fits of the fractal model to the light scattering data)
Figure 12B:
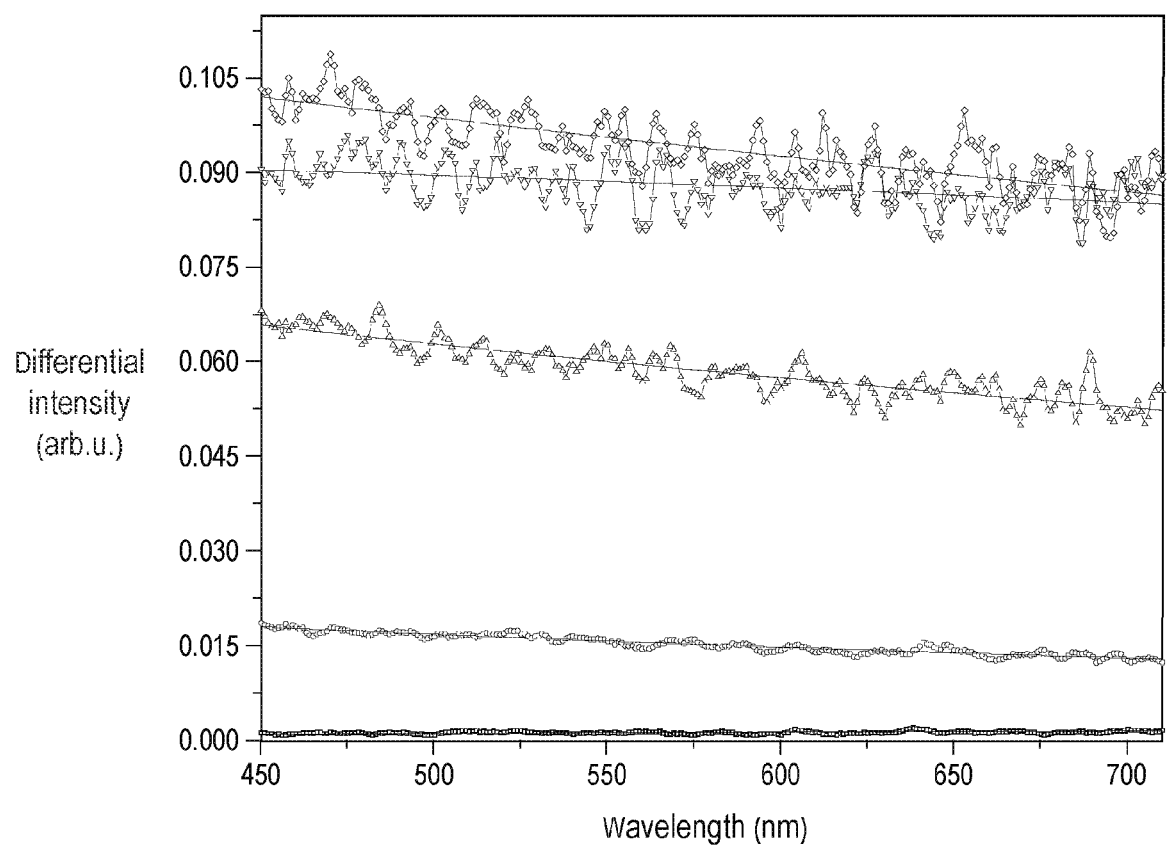
FIG. 12B is a light scattering spectroscopy (LSS) spectra of MeOH treated films at different cycles of mineralization (solid lines are fits of the fractal model to the light scattering data)
Figure 12C:
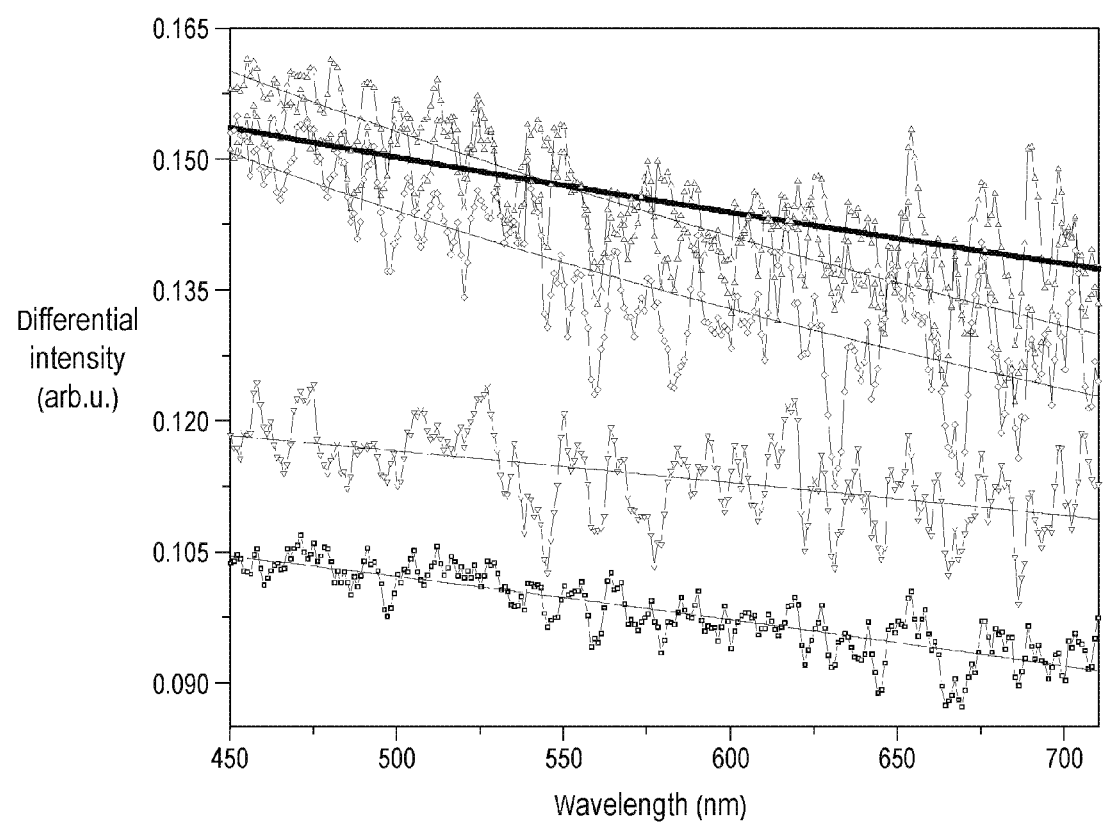
FIG. 12C is a light scattering spectroscopy (LSS) spectra of PAA mixed films at different cycles of mineralization (solid lines are fits of the fractal model to the light scattering data)
Figure 13A:
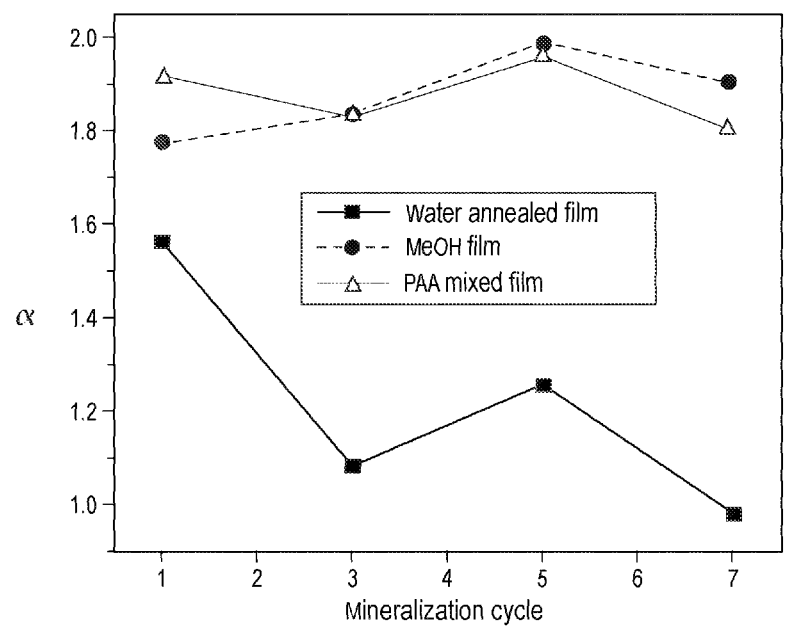
FIG. 13A is a graph of the fractal parameters 'α' versus mineralization cycle for water annealed, MeOH treated and PAA mixed silk films.
Figure 13B:
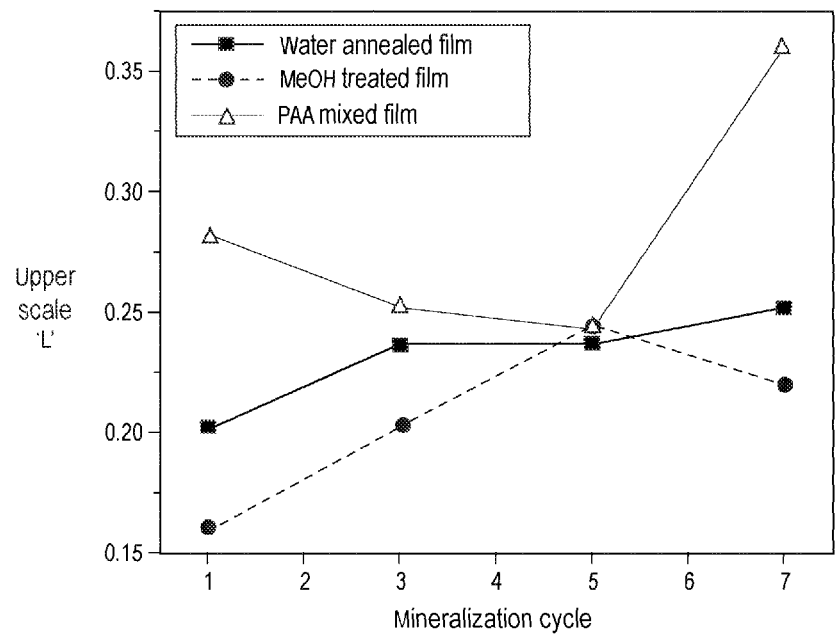
FIG. 13B is a graph of the upper scale 'L' versus mineralization cycle for water annealed, MeOH treated and PAA mixed silk films.
Figure 14A:
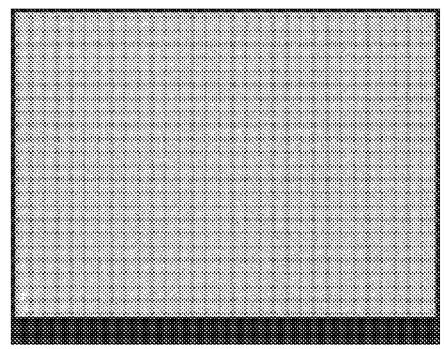
FIGS. 14A though 14E are SEM images of a water annealed film before mineralization (A), first cycle (B), third cycle (C), fifth cycle (D) and seventh cycle (E) of mineralization at 10000× resolution.
Figure 14B:
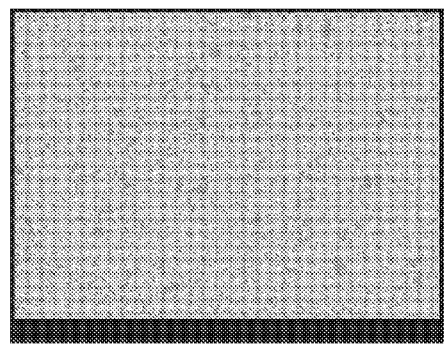
Figure 14C:
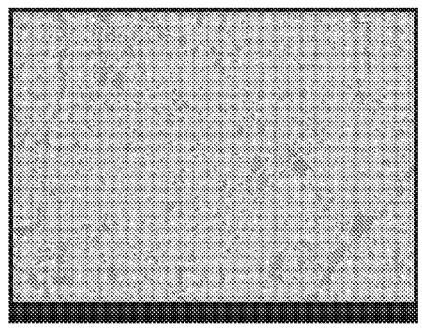
Figure 14D:
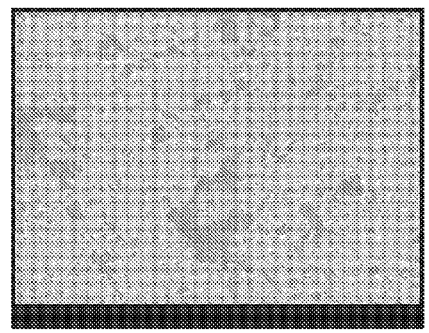
Figure 14E:
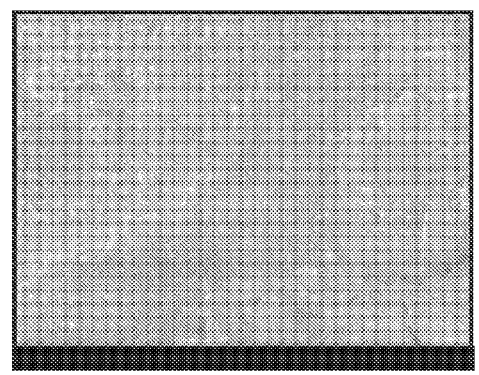
Figure 15A:
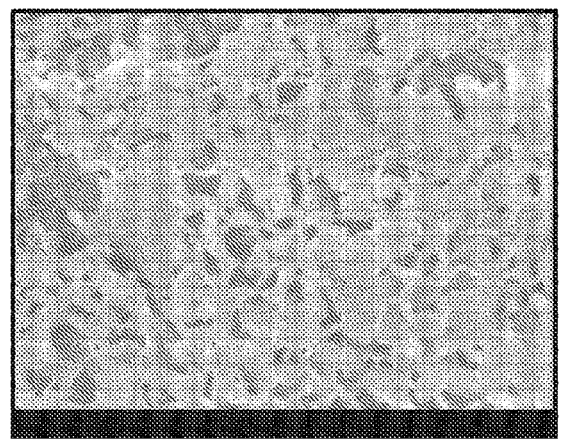
FIG. 15A-15C are SEM images of mineralized silk films, at 30000× magnification, after seventh cycle of mineralization. (A) Water-annealed, (B) Methanol-treated, (C) PAA-mixed.
Figure 15B:
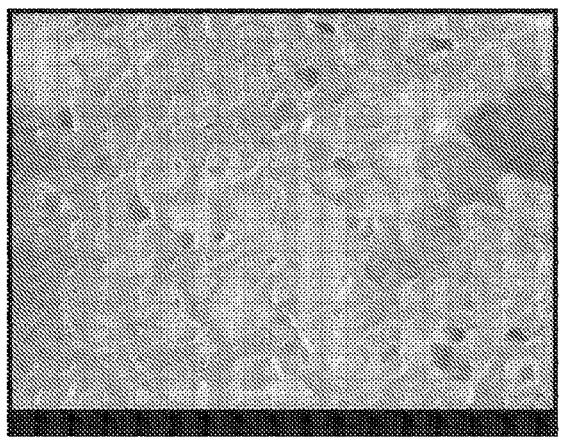
Figure 15C:
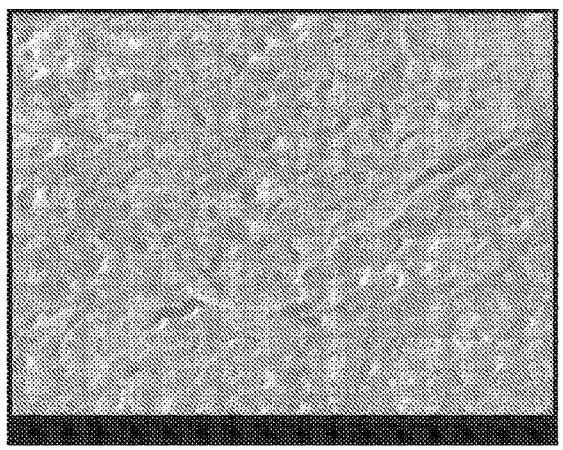
Figure 16:
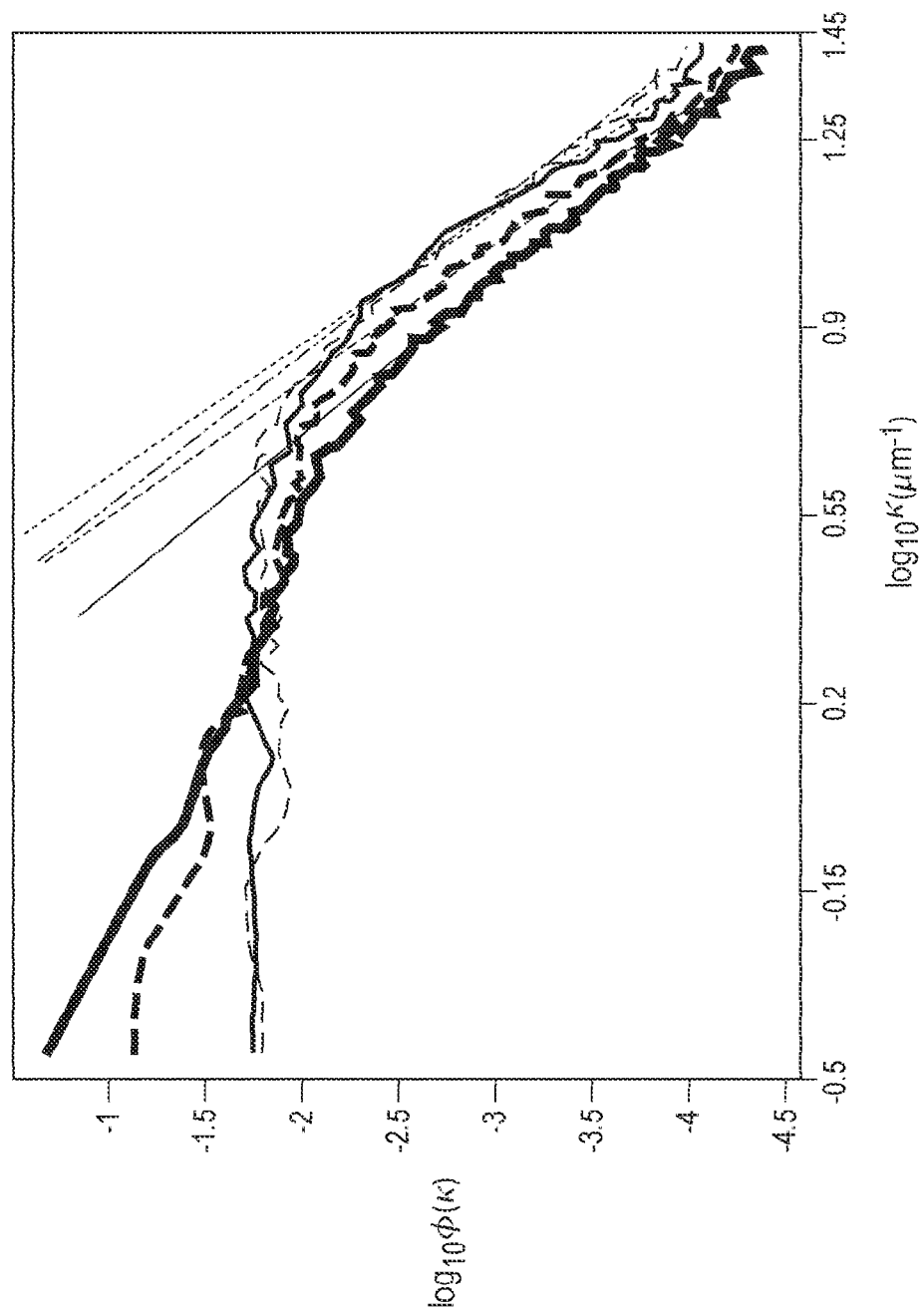
FIG. 16 is graph of the inverse power law fitted PSD profiles of 10000× water annealed mineralized silk films at first cycle (purple color), third cycle (green color), fifth cycle (black color) and seventh cycle (light green color) of mineralization.
Figure 17:
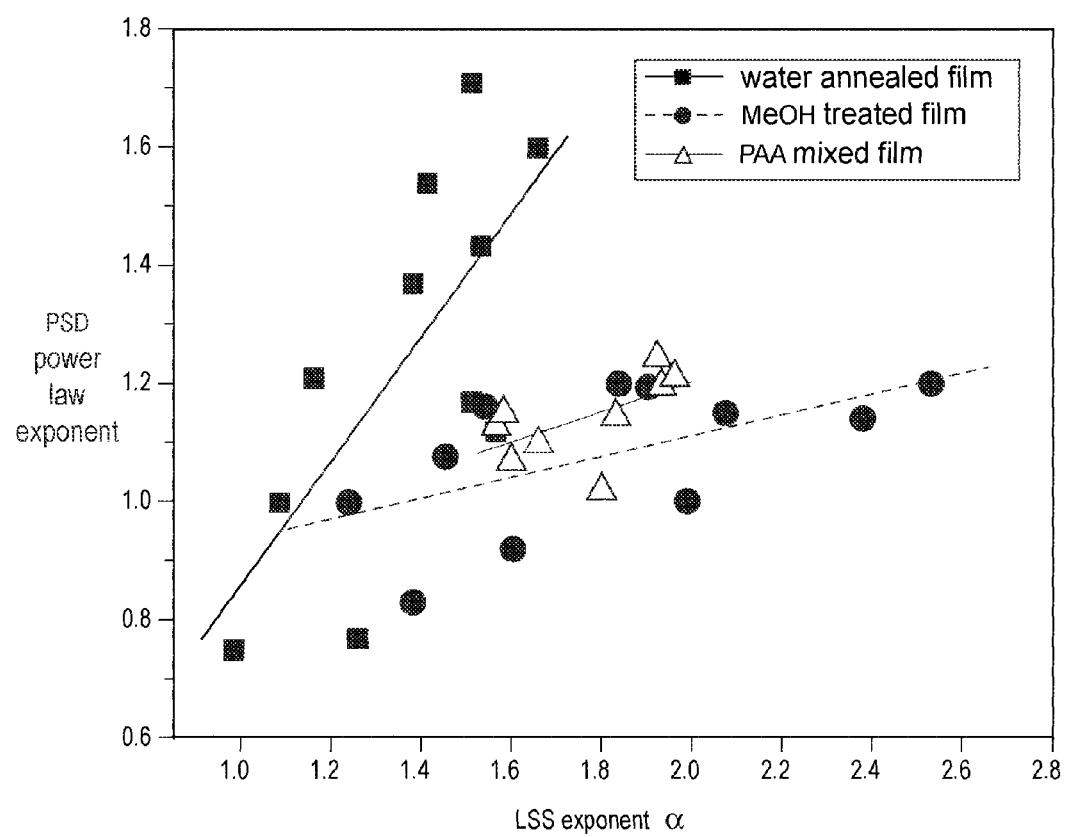
FIG. 17 is a graph of the PSD power law exponent versus LSS exponent α showing the correlation of light scattering slopes and PSD inverse power law slopes for different types of silk films water annealed (■ solid square, correlation coefficient 0.72), MeOH treated (● solid circles, correlation coefficient 0.59), PAA mixed silk films (▲ solid triangles, correlation coefficient 0.57).

The high frequency inverse power law behavior in the PSD functions of the SEM images is indicative of scale-invariant fractal organization (self-affinity) of the mineralized films' morphology at submicron scales, in accordance with the single-scattering LSS results discussed above. FIG. 9 includes the inverse power law fits to the PSD functions of water-annealed films over the high spatial frequency range $0.85\ \mu m^{-1}<\log_{10}\kappa<1.25\ \mu m^{-1}$. The PSD power exponents obtained from all the mineralized films are shown in FIG. 10, where they are plotted against the corresponding self-affine fractal power exponent, α, obtained by LSS. Significant correlation is observed between the SEM and LSS fractal power exponents, corroborating the sensitivity of the LSS technique to the fractal mineral morphology at submicron scales. The correlation coefficients for water annealed, MeOH treated and PAA mixed films were found to be R=0.72, 0.59 and 0.57 respectively.

It is interesting that in methanol-treated and PAA-mixed films, the relationship between LSS and SEM fractal exponents, α and δ, was very similar to each other, but quite different than in the water-annealed films (see slopes in FIG. 10). This is qualitatively in line with the different fractal parameters, H and $D_E$, inferred via LSS for water-annealed films on one hand, and methanol-treated and PAA-mixed films on the other. We note, however, that the relationship between LSS and SEM fractal parameters for all films shown in FIG. 10 is not in quantitative agreement with our LSS model for a weakly-scattering, self-affine substrate. According to eqns. 2 and 4, the relationship between α and δ is given by:

$$\delta = 2\alpha - D_E + 1 \quad (5)$$

The slopes for all films in FIG. 10, however, were all markedly lower than 2 and the y-intercepts were also not consistent with the inferred values of $D_E$ for these films. The discrepancy could be due to a variety of factors. If the differential LSS signal in these experiments, for example, is sensitive to deeper surface layers than assumed (depth>few hundred nm), the weak scattering (Born approximation) assumption would no longer be valid and our LSS model would need to be modified. Systematic errors in the PSD fractal exponents, δ, could have also resulted from contamination by the κ-dependent signal often seen at low spatial frequencies. Future work will address these issues by examining films at much lower stages of mineralization, to ensure low optical density of the films and to minimize LSS contributions from larger clumps (low spatial frequency) of deposited minerals.

Finally, the transition away from a power law PSD regime to a κ-independent, low frequency zone is indicative of an upper limit to the correlation distance over which fractal behavior is exhibited by these films (the fractal upper scale, L, discussed above). Although a precise characterization of these upper scales is not always possible from our PSD curves, due to the frequent presence of additional low-frequency components, an estimate can be made from the approximate position of the "elbow" in the PSD curves ($0.5 \mu m^{-1} < \log_{10} \kappa < 0.8 \mu m^{-1}$) [Schmitt J M, Kumar G. Turbulent nature of refractive-index variations in biological tissue. *Opt Lett* 1996;21: 1310-1312]. These spatial frequencies correspond to upper scale values in the range 150 nm<L<300 nm, which is in remarkably close agreement with the values obtained by LSS.

Hence, in some aspects, the invention provides a method of using LSS as a non-invasive technology to assess the amount and organization of mineral deposits in a sample (i.e., minerals deposited on silk films). The Examples demonstrate that the integrated intensity of backscattered light in the 450 to 700 nm region can be used to assess the overall amount of mineral deposited on the films, as confirmed by correlations with TGA measurements. The Examples show that the PAA-mixed films with the highest β sheet content yield enhanced levels of mineral deposition, when compared to methanol treated and water annealed films. The deposited minerals had a self-affine fractal morphology, with an upper limit to the range of fractal organization in all films in the range 150 nm<L<300 nm, as confirmed by both differential LSS and SEM analyses. Minerals on the water-annealed films were predominantly flake-like, with positively correlated height fluctuations within each flake (H>0.5), whereas methanol-treated and PAA-mixed silk films supported densely-packed, bulk mineral films with negatively correlated density fluctuations (H<0.5). LSS can also be used to characterize mineral deposition occurring at slower rates, which is relevant to biomaterial mineralization processes occurring naturally.

While the present invention has been described in terms of specific methods and compositions, it is understood that variations and modifications can be made without departing from the scope of the invention will occur to those skilled in the art upon consideration of the present invention. Those skilled in the art will appreciate, or be able to ascertain using no more than routine experimentation, further features and advantages of the invention based on the above-described embodiments. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from various aspects of the invention as defined in the claims. Accordingly, the invention is not to be limited by what has been particularly shown and described. All publications and references cited in the present application are herein expressly incorporated by reference in their entirety.

What is claimed is:

1. A method of monitoring mineralization in a sample, comprising
illuminating a sample with polarized radiation having at least two different wavelengths,
for each of the illuminating radiation wavelengths, detecting at least a portion of scattered radiation from the sample having a polarization parallel to said illuminating radiation and a portion having polarization perpendicular to the illuminating radiation in order to obtain a measurement of singly scattered radiation from the sample in response to said illumination at said two wavelengths, and
comparing intensities of said detected singly scattered radiation at said two wavelengths to obtain information regarding one or more mineral constituents of said sample.

2. The method of claim 1, further comprising calculating, for each of the wavelengths, a differential intensity of the detected scattered radiation at said parallel and perpendicular polarizations.

3. The method of claim 2, wherein said step of comparing intensities comprises comparing said differential intensity corresponding to one wavelength with the respective differential intensity corresponding to the other wavelength to obtain the information regarding said one or more mineral constituents of said sample.

4. The method of claim 1, wherein said information relates to a morphology of said one or more mineral constituents of the sample.

5. The method of claim 1, wherein said illuminating step comprises illuminating the sample concurrently with said two radiation wavelengths.

6. The method of claim 1, further comprising dispersing said scattered radiation to detect the scattered radiation at each of said wavelengths.

7. The method of claim 1, wherein said illuminating step comprises illuminating the sample with each of said wavelengths during different temporal intervals.

8. The method of claim 1, wherein said detecting step comprises detecting at least a portion of radiation elastically scattered from the sample.

9. A method of measuring a property of a sample, comprising
measuring a wavelength spectrum of singly elastically scattered radiation from a sample by illuminating the sample with polarized radiation having a plurality of wavelengths and detecting at least a portion of scattered radiation from the sample having a polarization parallel to said illuminating radiation and a portion having polarization perpendicular to the illuminating radiation in order to obtain a measurement of singly scattered radiation from the sample at each of the plurality of wavelengths, and
utilizing said wavelength spectrum to derive information regarding mineralization of said sample.

10. The method of claim 9, further comprising fitting said wavelength spectrum to a morphological mineralization model to derive information regarding morphology of mineral content of said sample.

11. The method of claim 9, further comprising integrating said wavelength spectrum to obtain information regarding an amount of mineral content of said sample.

12. The method of claim 9, wherein said detected scattered radiation comprises radiation elastically scattered from the sample.

13. A method of monitoring a sample, comprising
measuring scattered radiation from a sample in response to illumination by polarized radiation at a plurality of wavelengths and at a plurality of different scattering angles during each of a plurality of temporal intervals,
for each of said temporal intervals and for each of the illuminating radiation wavelengths, detecting at least a portion of scattered radiation from the sample having a polarization parallel to said illuminating radiation and a portion having a polarization perpendicular to the illuminating radiation in order to obtain a measurement of singly scattered radiation from the sample,
analyzing the measured singly scattered radiation as a function of wavelength and scattering angle to derive information regarding mineralization of the sample, and
comparing said information corresponding to different temporal intervals to monitor changes in the mineralization as a function of time.

14. The method of claim 13, wherein said step of measuring radiation comprises measuring radiation elastically scattered from the sample.

15. A method of characterizing mineralization, comprising
measuring backscattered radiation from a sample at two different polarizations in response to illumination of the sample with polarized radiation at a plurality of wavelengths in order to obtain a measurement of singly scattered radiation from the sample at each of the plurality of wavelengths,
obtaining a differential intensity of the measured backscattered radiation at said polarizations for said plurality of wavelengths,
analyzing said differential intensity as a function of wavelength to characterize mineralization of the sample.

16. The method of claim 15, wherein said step of characterizing the mineralization comprises obtaining information about morphology of mineral deposits.

17. The method of claim 15
wherein said analyzing step comprises utilizing a self-affine fractal model to derive information regarding morphology of the mineral deposits from said measured backscattered differential intensity.

18. The method of claim 17, wherein said self-affine fractal model is described by the following expression:

$$\Delta I(\lambda) \propto \lambda^{-4} \frac{1}{\left[1+\left(\frac{4\pi L}{\lambda}\right)^2\right]^\alpha}$$

wherein,
L represents the fractal upper scale (the upper bound of fractal correlation lengths) and
the exponent $\alpha$ is related to the Hurst parameter, H, via the following relation:

$H=\alpha-D_E/2$ wherein, $D_E$ is the Euclidean dimension of the scattering system.

19. The method of claim 18, wherein $D_E=1$ denotes a filamentous morphology for said mineral deposits.

20. The method of claim 18, wherein $D_E=2$ denotes a sheet-like morphology for said mineral deposits.

21. The method of claim 18, wherein $D_E=3$ denotes a bulk space-filling morphology.

22. The method of claim 15, wherein said step of measuring radiation comprises measuring radiation elastically backscattered from the sample.

* * * * *